US009109261B2

(12) United States Patent
Hogan et al.

(10) Patent No.: US 9,109,261 B2
(45) Date of Patent: *Aug. 18, 2015

(54) METHOD AND KIT FOR IDENTIFYING ANTIBIOTIC-RESISTANT MICROORGANISMS

(75) Inventors: James J. Hogan, Coronado, CA (US); Shannon K. Kaplan, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 310 days.

This patent is subject to a terminal disclaimer.

(21) Appl. No.: 12/774,229

(22) Filed: May 5, 2010

(65) Prior Publication Data

US 2010/0216155 A1    Aug. 26, 2010

Related U.S. Application Data

(63) Continuation of application No. 10/843,799, filed on May 11, 2004, now Pat. No. 7,786,289.

(60) Provisional application No. 60/469,997, filed on May 13, 2003, provisional application No. 60/516,100, filed on Oct. 31, 2003.

(51) Int. Cl.
*C12M 1/34* (2006.01)
*C07H 21/04* (2006.01)
*C12Q 1/68* (2006.01)

(52) U.S. Cl.
CPC .............. *C12Q 1/689* (2013.01); *C12Q 1/6837* (2013.01)

(58) Field of Classification Search
None
See application file for complete search history.

(56) References Cited

U.S. PATENT DOCUMENTS

| | | | | |
|---|---|---|---|---|
| 5,283,174 | A * | 2/1994 | Arnold et al. ............... | 435/6 |
| 5,437,978 | A | 8/1995 | Ubukata et al. | |
| 5,541,308 | A * | 7/1996 | Hogan et al. ............... | 536/23.1 |
| 5,547,842 | A | 8/1996 | Hogan et al. | |
| 5,582,974 | A * | 12/1996 | Nietuspki et al. ........... | 435/6 |
| 5,679,520 | A | 10/1997 | Hogan et al. | |
| 5,702,895 | A | 12/1997 | Matsunaga et al. | |
| 5,770,361 | A * | 6/1998 | Arthur et al. ............... | 435/6 |
| 5,770,373 | A | 6/1998 | Britschgi et al. | |
| 5,962,225 | A | 10/1999 | Ramberg | |
| 6,235,484 | B1 * | 5/2001 | Hogan et al. ............... | 435/6 |
| 6,312,960 | B1 * | 11/2001 | Balch et al. ............... | 506/32 |
| 6,406,892 | B1 | 6/2002 | Aberin et al. | |
| 6,458,540 | B1 | 10/2002 | Ramberg | |
| 6,503,709 | B1 * | 1/2003 | Bekkaoui et al. ........... | 435/6 |
| 6,582,908 | B2 | 6/2003 | Fodor | |
| 6,821,770 | B1 | 11/2004 | Hogan | |
| 2002/0106646 | A1 | 8/2002 | Remacle et al. | |
| 2003/0143571 | A1 * | 7/2003 | Sharp et al. ............... | 435/6 |

FOREIGN PATENT DOCUMENTS

| | | |
|---|---|---|
| EP | 1 136 566 A1 | 9/2001 |
| FR | 2 736 652 A | 1/1997 |
| WO | 99/16780 A2 | 4/1999 |
| WO | 01/12803 A2 | 2/2001 |
| WO | WO 01/12803 * | 2/2001 |
| WO | 01/23604 A2 | 4/2001 |
| WO | 02/082086 A2 | 10/2002 |
| WO | 03/033724 | 4/2003 |

OTHER PUBLICATIONS

GenBank Accession AR035505 GI 5952173 Sep. 29, 1999.*
GenBank Accession AR089432 GI 10016189 Sep. 7, 2000.*
Bergeron, Michael et al. Preventing antibiotic resistance through rapid genotypic identification of bacteria and of their antibiotic resistance genes in the clinical microbiology laboratory. 1998. Journal of Clinical Microbiology. vol. 36 No. 8 pp. 2169-2172.*
GenBank Accession AR089410 GI 10016167 Sep. 7, 2000.*
GenBank Accession AR035505 GI 5952173, Sep. 29, 1999.
GenBank Accession AR089432 GI 10016189, Sep. 7, 2000.
GenBank Accession AR089410 GI 10016167, Sep. 7, 2000.
Decision to Grant in Corresponding EP Application 04 775 973.3 dated Feb. 5, 2009 (96 pp).
Intl. Preliminary Report in Corresponding PCT Application PCT/US2004/014690 dated Dec. 1, 2005 (11 pp).
Written Opinion in Corresponding PCT Application PCT/US2004/014690 dated May 26, 2005 (9 pp).
Notice of Allowance received in corresponding JP Patent Application 2006-514343 dated Dec. 20, 2010.
Davis, "Direct Identification of Bacterial Isolates in Blood Cultures by Using a DNA Probe," J. Clin. Microbiology, Oct. 1991, 29(10):2193-2196, ASM, Washington, D.C., U.S.A.
Modrusan, "Detection of Vancomycin Resistant Genes vanA and vanB by Cycling Probe Technology," Mol. Cell. Probes, 1999, 13:223-231, Academic Press Limited, USA.
Moore, "A rapid molecular assay for the detection of antibiotic resistance determinants in causal agents of infective endocarditis," J. Appl. Microbiol., 2001, 90(5):719-726, ASM, Washington, D.C., U.S.A.
Notice of Reasons for Rejection, Japanese Patent Application No. 2010-265827, mailed Sep. 19, 2012.
Boyle-Vavra, "Transcriptional Induction of the Penicillin-Binding Protein 2 Gene in Staphylococcus aureus by Cell Wall-Active Antibiotics Oxacillin and Vancomycin," Antimicrobial Agents & Chemotherapy, Mar. 2003, 47 (3):1028-1036, American Society for Microbiology, Washington, D.C., U.S.A.
Centers for Disease Control and Prevention, "Staphylococcus aureus Resistant to Vancomycin—United States, 2002," Morbidity and Mortality Weekly Report, Jul. 5, 2002, 51(26):565-567, Atlanta, GA, U.S.A.
Centers for Disease Control and Prevention, "Vancomycin-Resistant *Staphylococcus aureus*—New York, 2004," Morbidity and Mortality Weekly Report, Apr. 23, 2004, 53(15):322-323, Atlanta, GA, U.S.A.
Cockerill, III, "Genetic Methods for Assessing Antimicrobial Resistance," Antimicrobial Agents & Chemotherapy, Feb. 1999, 43(2):199-212, American Society for Microbiology, Washington, D.C., U.S.A.

(Continued)

*Primary Examiner* — Amanda Haney
(74) *Attorney, Agent, or Firm* — Jeffrey E. Landes

(57) ABSTRACT

The invention provides a rapid sample-processing method for preparing hybridization reaction mixtures substantially depleted of RNA, and a method of identifying the methicillin-resistance status and vancomycin-resistance status of an organism.

15 Claims, No Drawings

(56) References Cited

OTHER PUBLICATIONS

Felten, "Evaluation of Three Techniques for Detection of Low-Level Methicillin-Resistant *Staphyloycoccus aureus* (MRSA): a Disk Diffusion Method with Cefoxitin and Moxalactam, the Vitek 2 System, and the MRSA-Screen Latex Agglutination Test," J. Clin. Microbiology, Aug. 2002, 40(8):2766-2771, ASM, Washington, D.C., U.S.A.

Geha, "Multiplex PCR for Identification of Methicillin-Resistant Staphylococci in the Clinical Laboratory," J.Clin. Microbiology, Jul. 1994 32(7):1768-1772, American Society for Microbiology, Washington, D.C., U.S.A.

Hogan, "Simultaneous Identification of Staphylococcus and mecA gene Using a Rapid DNA Probe Assay," Poster C-084, ASM Abstract Database ID #78960, 2003—103rd General Meeting of American Society for Microbiology, May 18, 2003-May 22, 2003, ASM, Washington, D.C., U.S.A.

Kolbert, "Detection of the *Staphylococcal* mecA Gene by Chemiluminescent DNA Hybridization," J. Clin. Microbiology, Aug. 1995, 33(8):2179-2182, American Society for Microbiology, Washington, D.C., U.S.A.

Murakami, "Identification of Methicillin-Resistant Strains of *Staphylococci* by Polymerase Chain Reaction," J. Clin. Microbiology, Oct. 1991, 29(10):2240-2244, American Society for Microbiology, Washington, D.C., U.S.A.

Pfaller, "Molecular Approaches to Diagnosing and Managing Infectious Diseases: Practicality and Costs," Emerging Infectious Diseases, Mar.-Apr. 2001, 7(2):312-318, Centers for Disease Control and Prevention, Atlanta, GA, U.S.A.

Skov, "Evaluation of a new 3-h hybridization method for detecting the mecA gene in *Staphylococcus aureus* and comparison with existing genotypic and phenotypic susceptibility testing methods," J. Antimicrobial Chemotherapy, 1999, 43:467-475, British Society for Antimicrobial Chemotherapy/Oxford Univ. Press, U.K.

Statens Serum Institut, "Evigene (TM)—MRSA Detection Kit," Version 2 (Date unknown), p. 1-15, Statens Serum Institut, Copenhagen, D.K.

Statens Serum Institut, "Evigene (TM)—VRE Detection Kit," Version 2, Sep. 2002, p. 1-15, Statens Serum Institut, Copenhagen, D.K.

Tang, "Molecular diagnostics of infectious diseases," Clin. Chemistry, 1997, 43(11):2021-2038, American Association for Clinical Chemistry, Washington, D.C., U.S.A.

Bergeron, "Preventing Antibiotic Resistance through Rapid Genotypic Identification of Bacteria and of Their Antibiotic Resistance Genes in the Clinical Microbiology Laboratory," J. Clin. Microbiology, Aug. 1998, 36(8):2169-2172, ASM, Washington, D.C., U.S.A.

Davies, "Inactivation of Antibiotics and the Dissemination of Resistance Genes," Science, Apr. 15, 1994, 264 (5157):375-381.

Dickinson, "Phenotypic Expression of Oaxacillin Resistance in *Staphylococcus* epidermidis: Roles of mecA Transcriptional Regulation and Resistant-Subpopulation Selection," Antimicrobial Agents & Chemotherapy, Jun. 2000, 44(6):1616-1623, ASM, Washington, D.C., U.S.A.

Fong, "Rapid Solid-Phase Immunoassay for Detection of Methicillin-Resistant *Staphylococcus aureus* Using Cycling Probe Technology," J. Clin. Microbiology, Jul. 2000, 38(7):2525-2529, ASM, Washington, D.C., U.S.A.

Hakenbeck, "Resistant penicillin-binding proteins," Cell. Mol. Life Sci., 1998, 54:332-340, Birkhauser Verlag, Basel, Switzerland.

Hallin, "Clinical Impact of a PCR Assay for Identification of *Staphylococcus aureus* and Determination of Methicillin Resistance Directly from Blood Cultures," J. Clin. Microbiology, Aug. 2003, 41(8):3942-3944, ASM, Washington, D.C., U.S.A.

Hamels, "Consensus PCR and Microarray for Diagnosis of the Genus *Staphylococcus*, Species and Methicillin Resistance," BioTechniques, Dec. 2001, 31(6):1364-1372, BioTechniques, Westborough, MA, U.S.A.

Henry, "Antibiotic Resistance," C&EN, Mar. 6, 2000, 78(10):41-58, American Chemical Society, Washington, D.C., U.S.A.

Hussain, "Rapid Detection of mecA-Positive and mecA-Negative Coagulase-Negative *Staphylococci* by an Anti-Penicillin Binding Protein 2a Slide Latex Agglutination Test," J. Clin. Microbiology, Jun. 2000, 38(6):2051-2054, American Society for Microbiology, Washington, D.C., U.S.A.

Jaffe, "Rapid Extraction from and Direct Identification in Clinical Samples of Methicillin-Resistant *Staphylococci* Using the PCR," J. Clin. Microbiology, Sep. 2000, 38(9):3407-3412, American Society for Microbiology, Washington, D.C., U.S.A.

Jorgensen, "Antimicrobial Susceptibility Testing: Special Needs for Fastidious Organisms and Difficult-to-Detect Resistance Mechanisms," Clin. Infectious Diseases, 2000, 30:799-808, Infectious Diseases Society of America/Univ. of Chicago, Chicago, IL, U.S.A.

Kohner, "Comparison of Susceptibility Testing Methods with mecA Gene Analysis for Determining Oxacillin.(Methicillin) Resistance in Clinical Isolates of *Staphylococcus areus* and Coagulase-Negative *Staphylococcus* spp." J. Clin. Microbiology, Sep. 1999, 37(9):2952-2961, ASM, Washington, D.C., U.S.A.

Kolbert, "Branched-DNA Assay for Detection of the mecA Gene in Oxacillin-Resistant and Oxacillin-Sensitive *Staphylococci*," J. Clin. Microbiology, Sep. 1998, 36(9):2640-2644, ASM, Washington, D.C., U.S.A.

Martineau, "Correlation between the Resistance Genotype Determined by Multiplex PCR Assays and the Antibiotic Susceptibility Patterns of *Staphylococcus* epidermidis," Antimicrobial Agents & Chemotherapy, Feb. 2000, 44 (2):231-238, ASM, Washington, D.C., U.S.A.

Merlino, "New Chromogenic Identification and Detection of *Staphylococcus aureus* and Methicillin-Resistant *S. aureus*," J. Clin. Microbiology, Jun. 2000, 38(6):2378-2380, ASM, Washington, D.C., U.S.A.

Oliveira, "Direct Identification of *Staphylococcus aureus* from Positive Blood Culture Bottles," J. Clin. Microbiology, Feb. 2003, 41(2):889-891, ASM, Washington, D.C., U.S.A.

Oliveira, "Genetic Organization of the Downstream Region of the mecA Element in Methicillin-Resistant *Staphylococcus aureus* Isolates Carrying Different Polymorphisms of This Region," Antimicrobial Agents & Chemotherapy, Jul. 2000, 44(7):1906-1910, British Society for Antimicrobial Chemotherapy/Oxford Univ. Press, U.K.

Poulsen, "Detection of Low-Level Methicillin-Resistant *Staphylococcus aureus* with Commercially Available Tests," J. Clin. Microbiology, Jul. 2003, 41(7):3458, ASM, Washington, D.C., U.S.A.

Poulsen, "Detection of methicillin resistance in coagulase-negative *staphylococci* and in *staphylococci* directly from simulated blood cultures using the Evigene MRSA Detection Kit," J. Antimicrobial Chemotherapy, 2003, 51:419-421, British Society for Antimicrobial Chemotherapy/Oxford Univ. Press, U.K.

Reischl, "Rapid Identification of Methicillin-Resistant *Staphylococcus aureus* and Simultaneous Species Confirmation Using Real-Time Fluorescence PCR," J. Clin. Microbiology, Jun. 2000, 38(6):2429-2433, ASM, Washington, D.C., U.S.A.

Schmitz, "Prevalence of macrolide-resistance genes in *Staphylococcus aureus* and *Enterococcus faecium* isolates from 24 European university hospitals," J. Antimicrobial Chemotherapy, 2000, 45:891-894, British Society for Antimicrobial Chemotherapy/Oxford Univ. Press, U.K.

Shopsin, "Use of Coagulase Gene (coa) Repeat Region Nucleotide Sequences for Typing of Methicillin-Resistant *Staphylococcus aureus* Strains," J. Clin. Microbiology, Sep. 2000, 38(9):3453-3456, ASM, Washington, D.C., U.S.A.

Ubukata, "Rapid Detection of the mecA Gene in Methicillin-Resistant *Staphylococci* by Enzymatic Detection of Polymerase Chain Reaction Products," J. Clin. Microbiology, Jul. 1992, 30(7):1728-1733, ASM, Washington, D.C., U.S.A.

Witte, "Antibiotic resistance in Gram-positive bacteria: epidemiological aspects," J. Antimicrobial Chemotherapy, 1999, 44(Topic A):1-9, British Society for Antimicrobial Chemotherapy/Oxford Univ. Press, U.K.

Wu, "Genetic Organization of the mecA Region in Methicillin-Susceptible and Methicillin-Resistant Strains of *Staphylococcus sciuri*," J. Bacteriology, Jan. 1998, 180(2):236-242, ASM, Washington, D.C., U.S.A.

(56) References Cited

OTHER PUBLICATIONS

Zheng, "Direct mecA Detection from Blood Culture Bottles by Branched-DNA Signal Amplification," J. Clin. Microbiology, Dec. 1999, 37(12):4192-4193, ASM, Washington, D.C., U.S.A.

Chambers, "Penicillin-Binding Protein—Mediated Resistance in Pneumococci and *Staphylococci*," J. Infectious Diseases, 1999, 179(Suppl 2):S353-S359, Infectious Diseases Society of America/Univ. of Chicago, Chicago, IL, USA.

Larsen, "Evaluation of the evigene VRE detection kit for the detection of enterococci harboring the vancomycin resistance genes vanA and vanB," Clin. Microbiology & Infection, 2001, 7(Suppl 1):Abstract and Poster P506, Blackwell Publishing for European Society of Clinical Microbiology and Infectious Diseases, Oxford, U.K.

Anthony et al., "Direct detection of *Staphylococcus aureus* mRNA using a flow through microarray", 2005, J. Microbiol. Methods, 60:47-54, Elsevier, The Netherlands.

Ito et al., "Structural Comparison of Three Types of Staphylococcal Cassette Chromosome mec Integrated in the Chromosome in Methicillin-Resistant *Staphylococcus aureus*", 2001, Antimicrob. Agents Chemother., 45 (5):1323-1336, ASM USA.

Patel et al., "DNA Sequence Variation within vanA, vanB, vanC-1 and vanC-2/3 Genes of Clinical Enterococcus Isolates", 1998, Antimicrob. Agents Chemother., 42(1):202-205, ASM, USA.

Westin et al., "Antimicrobial Resistance and Bacterial Identification Utilizing a Microelectronic Chip Array", 2001, J. Clin. Microbiol., 39(3):1097-1104, ASM, USA.

Shi et al. "DNA Extraction from Archival Formalin-fixed, Paraffin-embedded Tissue Sections Based on the Antigen Retrieval Principle: Heating Under the Influence of pH", J Histochem Cytochem, 2002, 50(8):1005-1011, The Histochemical Society, Inc.

Bergeron et al., Preventing Antibiotic Resistance Using Rapid DNA Based Diagnostics, Aug. 1998, Infection Control and Hospital Epidemiology., vol. 19(8), pp. 560-564.

Ke, Danbing et al., "Development of a PCR assay for rapid detection of Enterococci," 1999, J. Clinical Microbiology, vol. 37(11), pp. 3497-3503, ASM, USA.

\* cited by examiner

SEQUENCE LISTING

```
<160> NUMBER OF SEQ ID NOS: 41

<210> SEQ ID NO 1
<211> LENGTH: 31
<212> TYPE: DNA
<213> ORGANISM: Staphylococcus aureus
<220> FEATURE:
<221> NAME/KEY: misc_feature
<222> LOCATION: (1)...(31)
<223> OTHER INFORMATION: mecA sequence

<400> SEQUENCE: 1
ggtatgtgga agttagattg ggatcatagc g                              31

<210> SEQ ID NO 2
<211> LENGTH: 31
<212> TYPE: DNA
<213> ORGANISM: Staphylococcus aureus
<220> FEATURE:
<221> NAME/KEY: misc_feature
<222> LOCATION: (1)...(31)
<223> OTHER INFORMATION: mecA sequence

<400> SEQUENCE: 2
cgctatgatc ccaatctaac ttccacatac c                              31

<210> SEQ ID NO 3
<211> LENGTH: 35
<212> TYPE: DNA
<213> ORGANISM: Staphylococcus aureus
<220> FEATURE:
<221> NAME/KEY: misc_feature
<222> LOCATION: (1)...(35)
<223> OTHER INFORMATION: mecA sequence

<400> SEQUENCE: 3
gcgataatgg tgaagtagaa atgactgaac gtccg                          35

<210> SEQ ID NO 4
<211> LENGTH: 35
<212> TYPE: DNA
<213> ORGANISM: Staphylococcus aureus
<220> FEATURE:
<221> NAME/KEY: misc_feature
<222> LOCATION: (1)...(35)
<223> OTHER INFORMATION: mecA sequence

<400> SEQUENCE: 4
cggacgttca gtcatttcta cttcaccatt atcgc                          35

<210> SEQ ID NO 5
<211> LENGTH: 35
<212> TYPE: DNA
<213> ORGANISM: Staphylococcus aureus
<220> FEATURE:
<221> NAME/KEY: misc_feature
<222> LOCATION: (1)...(35)
<223> OTHER INFORMATION: mecA sequence

<400> SEQUENCE: 5
gctccaacat gaagatggct atcgtgtcac aatcg                          35
```

<210> SEQ ID NO 6
<211> LENGTH: 35
<212> TYPE: DNA
<213> ORGANISM: Staphylococcus aureus
<220> FEATURE:
<221> NAME/KEY: misc_feature
<222> LOCATION: (1)...(35)
<223> OTHER INFORMATION: mecA sequence

<400> SEQUENCE: 6
cgattgtgac acgatagcca tcttcatgtt ggagc                              35

<210> SEQ ID NO 7
<211> LENGTH: 30
<212> TYPE: DNA
<213> ORGANISM: Staphylococcus aureus
<220> FEATURE:
<221> NAME/KEY: misc_feature
<222> LOCATION: (1)...(30)
<223> OTHER INFORMATION: Staphylococcus aureus probe

<400> SEQUENCE: 7
ccactcaaga gagacaacat tttcgactac                                    30

<210> SEQ ID NO 8
<211> LENGTH: 33
<212> TYPE: DNA
<213> ORGANISM: Staphylococcus aureus
<220> FEATURE:
<221> NAME/KEY: misc_feature
<222> LOCATION: (1)...(33)
<223> OTHER INFORMATION: Helper for S. aureus probe

<400> SEQUENCE: 8
gatgattcgt ctaatgtcga cctttgtaac tcc                                33

<210> SEQ ID NO 9
<211> LENGTH: 32
<212> TYPE: DNA
<213> ORGANISM: Staphylococcus aureus
<220> FEATURE:
<221> NAME/KEY: misc_feature
<222> LOCATION: (1)...(32)
<223> OTHER INFORMATION: Helper for S. aureus probe

<400> SEQUENCE: 9
cggaatttca cgtgctccgt cgtactcagg at                                 32

<210> SEQ ID NO 10
<211> LENGTH: 30
<212> TYPE: DNA
<213> ORGANISM: Staphylococcus aureus
<220> FEATURE:
<221> NAME/KEY: misc_feature
<222> LOCATION: (1)...(30)
<223> OTHER INFORMATION: Staphylococcus genus probe

<400> SEQUENCE: 10
ccgaactgag aacaacttta tgggatttgc                                    30

<210> SEQ ID NO 11
<211> LENGTH: 17
<212> TYPE: RNA
<213> ORGANISM: Staphylococcus aureus
<220> FEATURE:
<221> NAME/KEY: misc_feature
<222> LOCATION: (1)...(17)

```
<223> OTHER INFORMATION: Helper for Staphylococcus genus probe
<221> NAME/KEY: misc_feature
<222> LOCATION: (1)...(17)
<223> OTHER INFORMATION: 2'-methoxy backbone

<400> SEQUENCE: 11
uugaccucgc gguuucg                                                    17

<210> SEQ ID NO 12
<211> LENGTH: 39
<212> TYPE: DNA
<213> ORGANISM: Staphylococcus aureus
<220> FEATURE:
<221> NAME/KEY: misc_feature
<222> LOCATION: (1)...(39)
<223> OTHER INFORMATION: Helper for Staphylococcus genus probe

<400> SEQUENCE: 12
gcgattccag cttcatgtag tcgagttgca gactacaat                            39

<210> SEQ ID NO 13
<211> LENGTH: 86
<212> TYPE: DNA
<213> ORGANISM: Staphylococcus aureus
<220> FEATURE:
<221> NAME/KEY: misc_feature
<222> LOCATION: (1)...(86)
<223> OTHER INFORMATION: Staphylococcus genus target domain

<400> SEQUENCE: 13
gcgattccag cttcatgtag tcgagttgca gactacaatc cgaactgaga acaactttat     60
gggatttgct tgacctcgcg gtttcg                                          86

<210> SEQ ID NO 14
<211> LENGTH: 24
<212> TYPE: DNA
<213> ORGANISM: Enterococcus pseudoavium
<220> FEATURE:
<221> NAME/KEY: misc_feature
<222> LOCATION: (1)...(24)
<223> OTHER INFORMATION: Enterococcus spp. probe

<400> SEQUENCE: 14
ctcctaggtg ccagtcaaat tttg                                            24

<210> SEQ ID NO 15
<211> LENGTH: 21
<212> TYPE: DNA
<213> ORGANISM: Enterococcus faecalis
<220> FEATURE:
<221> NAME/KEY: misc_feature
<222> LOCATION: (1)...(21)
<223> OTHER INFORMATION: Enterococcus spp. probe

<400> SEQUENCE: 15
catcattctc aattccgagg c                                               21

<210> SEQ ID NO 16
<211> LENGTH: 16
<212> TYPE: DNA
<213> ORGANISM: Escherichia coli
<220> FEATURE:
<221> NAME/KEY: misc_feature
<222> LOCATION: (1)...(16)
<223> OTHER INFORMATION: Pan-bacterial probe

<400> SEQUENCE: 16
```
cgacaaggaa tttcgc                                                          16

<210> SEQ ID NO 17
<211> LENGTH: 17
<212> TYPE: DNA
<213> ORGANISM: Escherichia coli
<220> FEATURE:
<221> NAME/KEY: misc_feature
<222> LOCATION: (1)...(17)
<223> OTHER INFORMATION: Helper for pan-bacterial probe

<400> SEQUENCE: 17
taccttagga ccgttat                                                         17

<210> SEQ ID NO 18
<211> LENGTH: 16
<212> TYPE: DNA
<213> ORGANISM: Escherichia coli
<220> FEATURE:
<221> NAME/KEY: misc_feature
<222> LOCATION: (1)...(16)
<223> OTHER INFORMATION: Helper for pan-bacterial probe

<400> SEQUENCE: 18
caggtcggaa cttacc                                                          16

<210> SEQ ID NO 19
<211> LENGTH: 35
<212> TYPE: DNA
<213> ORGANISM: Escherichia coli
<220> FEATURE:
<221> NAME/KEY: misc_feature
<222> LOCATION: (1)...(35)
<223> OTHER INFORMATION: Pan-bacterial probe

<400> SEQUENCE: 19
ggaacttacc cgacaaggaa tttcgctacc ttagg                                     35

<210> SEQ ID NO 20
<211> LENGTH: 36
<212> TYPE: DNA
<213> ORGANISM: Escherichia coli
<220> FEATURE:
<221> NAME/KEY: misc_feature
<222> LOCATION: (1)...(36)
<223> OTHER INFORMATION: Helper for pan-bacterial probe

<400> SEQUENCE: 20
accgttatag ttacggccgc cgtttactgg ggcttc                                    36

<210> SEQ ID NO 21
<211> LENGTH: 32
<212> TYPE: DNA
<213> ORGANISM: Escherichia coli
<220> FEATURE:
<221> NAME/KEY: misc_feature
<222> LOCATION: (1)...(32)
<223> OTHER INFORMATION: Helper for pan-bacterial probe

<400> SEQUENCE: 21
gcctggccat cgttacgcca ttcgtgcagg tc                                        32

<210> SEQ ID NO 22
<211> LENGTH: 30
<212> TYPE: DNA
<213> ORGANISM: Staphylococcus aureus
<220> FEATURE:
<221> NAME/KEY: misc_feature

```
<222> LOCATION: (1)..(30)
<223> OTHER INFORMATION: Helper for pan-bacterial probe

<400> SEQUENCE: 22
gcccaaatcg ttacgccttt cgtgcgggtc                                    30

<210> SEQ ID NO 23
<211> LENGTH: 31
<212> TYPE: DNA
<213> ORGANISM: Enterococcus avium
<220> FEATURE:
<221> NAME/KEY: misc_feature
<222> LOCATION: (1)..(31)
<223> OTHER INFORMATION: Helper for Enterococcus spp. probe

<400> SEQUENCE: 23
tctacggggc ttttacccctt tctagcagac c                                  31

<210> SEQ ID NO 24
<211> LENGTH: 26
<212> TYPE: DNA
<213> ORGANISM: Enterococcus pseudoavium
<220> FEATURE:
<221> NAME/KEY: misc_feature
<222> LOCATION: (1)..(26)
<223> OTHER INFORMATION: Helper for Enterococcus spp. probe

<400> SEQUENCE: 24
cctcgtgttc cgccgtactc aggatc                                        26

<210> SEQ ID NO 25
<211> LENGTH: 38
<212> TYPE: DNA
<213> ORGANISM: Enterococcus faecium
<220> FEATURE:
<221> NAME/KEY: misc_feature
<222> LOCATION: (1)..(38)
<223> OTHER INFORMATION: Helper for Enterococcus spp. probe

<400> SEQUENCE: 25
tagccctaaa gctatttcgg agagaaccag ctatctcc                            38

<210> SEQ ID NO 26
<211> LENGTH: 26
<212> TYPE: DNA
<213> ORGANISM: Enterococcus faecium
<220> FEATURE:
<221> NAME/KEY: misc_feature
<222> LOCATION: (1)..(26)
<223> OTHER INFORMATION: Helper for Enterococcus spp. probe

<400> SEQUENCE: 26
ccctagtcca aacagtgctc tacctc                                        26

<210> SEQ ID NO 27
<211> LENGTH: 29
<212> TYPE: DNA
<213> ORGANISM: Enterococcus faecium
<220> FEATURE:
<221> NAME/KEY: misc_feature
<222> LOCATION: (1)..(29)
<223> OTHER INFORMATION: Van A sequence

<400> SEQUENCE: 27
gggttgctca gaggagcatg acgtatcgg                                     29

<210> SEQ ID NO 28
```

```
<210> SEQ ID NO 28
<211> LENGTH: 23
<212> TYPE: DNA
<213> ORGANISM: Enterococcus faecium
<220> FEATURE:
<221> NAME/KEY: misc_feature
<222> LOCATION: (1)...(23)
<223> OTHER INFORMATION: Van A sequence

<400> SEQUENCE: 28
gctgagcttt gaatatcgca gcc                                              23

<210> SEQ ID NO 29
<211> LENGTH: 20
<212> TYPE: DNA
<213> ORGANISM: Enterococcus faecium
<220> FEATURE:
<221> NAME/KEY: misc_feature
<222> LOCATION: (1)...(20)
<223> OTHER INFORMATION: Van A sequence

<400> SEQUENCE: 29
cgttcagtac aatgcggccg                                                  20

<210> SEQ ID NO 30
<211> LENGTH: 28
<212> TYPE: DNA
<213> ORGANISM: Enterococcus faecalis
<220> FEATURE:
<221> NAME/KEY: misc_feature
<222> LOCATION: (1)...(28)
<223> OTHER INFORMATION: Van B sequence

<400> SEQUENCE: 30
ccgcagcttg catggacaaa tcactggc                                         28

<210> SEQ ID NO 31
<211> LENGTH: 25
<212> TYPE: DNA
<213> ORGANISM: Enterococcus faecalis
<220> FEATURE:
<221> NAME/KEY: misc_feature
<222> LOCATION: (1)...(25)
<223> OTHER INFORMATION: Van B sequence

<400> SEQUENCE: 31
cgcatccatc aggaaaacga gccgg                                            25

<210> SEQ ID NO 32
<211> LENGTH: 27
<212> TYPE: DNA
<213> ORGANISM: Enterococcus faecalis
<220> FEATURE:
<221> NAME/KEY: misc_feature
<222> LOCATION: (1)...(27)
<223> OTHER INFORMATION: Van B sequence

<400> SEQUENCE: 32
ccaagcaccc gatatacttt ctttgcc                                          27

<210> SEQ ID NO 33
<211> LENGTH: 23
<212> TYPE: DNA
<213> ORGANISM: Enterococcus faecalis
<220> FEATURE:
<221> NAME/KEY: misc_feature
<222> LOCATION: (1)...(23)
<223> OTHER INFORMATION: Van A and Van B sequence

<400> SEQUENCE: 33
```

```
gagctttgaa tatcgcagcc tac                                              23

<210> SEQ ID NO 34
<211> LENGTH: 20
<212> TYPE: DNA
<213> ORGANISM: Enterococcus faecalis
<220> FEATURE:
<221> NAME/KEY: misc_feature
<222> LOCATION: (1)...(20)
<223> OTHER INFORMATION: Core sequence shared by VanA(-)792 and
      VanA&B(-)734

<400> SEQUENCE: 34
gagctttgaa tatcgcagcc                                                  20

<210> SEQ ID NO 35
<211> LENGTH: 26
<212> TYPE: DNA
<213> ORGANISM: Enterococcus faecium
<220> FEATURE:
<221> NAME/KEY: misc_feature
<222> LOCATION: (1)...(26)
<223> OTHER INFORMATION: Composite sequence containing the core
      sequence of SEQ ID NO:34

<400> SEQUENCE: 35
gctgagcttt gaatatcgca gcctac                                           26

<210> SEQ ID NO 36
<211> LENGTH: 38
<212> TYPE: DNA
<213> ORGANISM: Artificial Sequence
<220> FEATURE:
<223> OTHER INFORMATION: PCR primer for amplifying Van A sequences
<221> NAME/KEY: misc_feature
<222> LOCATION: (10)...(38)
<223> OTHER INFORMATION: Van A sequence

<400> SEQUENCE: 36
cggggtaccg ggttgctcag aggagcatga cgtatcgg                              38

<210> SEQ ID NO 37
<211> LENGTH: 28
<212> TYPE: DNA
<213> ORGANISM: Artificial Sequence
<220> FEATURE:
<223> OTHER INFORMATION: PCR primer for amplifying Van A sequences
<221> NAME/KEY: misc_feature
<222> LOCATION: (9)...(28)
<223> OTHER INFORMATION: Van A sequence

<400> SEQUENCE: 37
cgcggatccg ttcagtacaa tgcggccg                                         28

<210> SEQ ID NO 38
<211> LENGTH: 35
<212> TYPE: DNA
<213> ORGANISM: Artificial Sequence
<220> FEATURE:
<223> OTHER INFORMATION: PCR primer for amplifying Van B sequences
<221> NAME/KEY: misc_feature
<222> LOCATION: (8)...(35)
<223> OTHER INFORMATION: Van B sequence

<400> SEQUENCE: 38
cggggtaccg cagcttgcat ggacaaatca ctggc                                 35
```

```
<210> SEQ ID NO 39
<211> LENGTH: 34
<212> TYPE: DNA
<213> ORGANISM: Artificial Sequence
<220> FEATURE:
<223> OTHER INFORMATION: PCR primer for amplifying Van B sequences
<221> NAME/KEY: misc_feature
<222> LOCATION: (6)...(34)
<223> OTHER INFORMATION: Van B sequence

<400> SEQUENCE: 39
cgcggatcca agcacccgat atactttctt tgcc                              34

<210> SEQ ID NO 40
<211> LENGTH: 25
<212> TYPE: DNA
<213> ORGANISM: Enterococcus faecalis
<220> FEATURE:
<221> NAME/KEY: misc_feature
<222> LOCATION: (1)...(25)
<223> OTHER INFORMATION: Van B sequence

<400> SEQUENCE: 40
ccggctcgtt ttcctgatgg atgcg                                        25

<210> SEQ ID NO 41
<211> LENGTH: 27
<212> TYPE: DNA
<213> ORGANISM: Enterococcus faecalis
<220> FEATURE:
<221> NAME/KEY: misc_feature
<222> LOCATION: (1)...(27)
<223> OTHER INFORMATION: Van B sequence

<400> SEQUENCE: 41
ggcaaagaaa gtatatcggg tgcttgg                                      27
```

METHOD AND KIT FOR IDENTIFYING ANTIBIOTIC-RESISTANT MICROORGANISMS

RELATED APPLICATION

This application claims the benefit of priority of U.S. Provisional Application No. 60/469,997, filed May 13, 2003, and U.S. Provisional Application No. 60/516,100, filed Oct. 31, 2003, and is a continuation of U.S. application Ser. No. 10/843,799, now U.S. Pat. No. 7,786,289, filed May 11, 2004. The entire disclosure of these prior applications is hereby incorporated by reference.

FIELD OF THE INVENTION

The present invention relates to the field of nucleic acid diagnostics. More particularly, the invention relates to methods and compositions for detecting and identifying methicillin-resistant and/or vancomycin-resistant microorganisms.

BACKGROUND OF THE INVENTION

Procedures for detecting and identifying infectious organisms are some of the most critical tasks performed in the clinical laboratory. Whereas laboratory diagnoses of infectious diseases formerly were made by experienced microbiologists using visual inspection of stained clinical material, more rapid and objective results are obtainable using modem techniques. Immunoassays, including radioimmunoassays, enzyme-linked immunoassays, and latex agglutination and immunoblotting assays have developed into powerful diagnostic tools having utilities that are enhanced by the availability of monoclonal antibodies. Nucleic acid hybridization assays have been developed to detect microorganisms, and more recent advances in signal and target amplification have introduced the era of molecular diagnostics based on the use of oligonucleotide probes. Generally, a probe is a single-stranded polynucleotide having some degree of complementarity with a nucleic acid sequence that is to be detected ("target sequence"). A double-stranded nucleic acid hybrid between the probe and the target sequence results if the target sequence is contacted under hybridization-promoting conditions with a probe having a sufficient number of contiguous bases complementary to the target sequence. DNA/DNA, RNA/DNA or RNA/RNA hybrids may thus be formed under appropriate conditions. Probes commonly are labeled with a detectable moiety such as a radioisotope, a ligand, or a colorimetric, fluorometric or chemiluminescent moiety to facilitate the detection of hybrids. Indeed, clinical microbiologists now use an extensive array of techniques for identifying infectious organisms (see Manual of Clinical Microbiology Murray et al., eds., 6th edition, ASM Press (1995)). Automated substrate utilization systems typically rely on enzymatic reactions that release chromogenic or fluorogenic compounds, tetrazolium-based indicators of metabolic activity in the presence of different carbon sources, or detection of the acid products of metabolism. The patterns of positive and negative reactions with these substrates establish a biochemical profile that can be used to identify microorganisms isolated from clinical samples. The chromatographic profiles of the more than 300 fatty acids that contribute to the formation of lipids in bacteria and yeast have also been used to phenotype microorganisms. Despite the availability of these very powerful techniques, polynucleotide-based assays are rapidly gaining popularity in clinical laboratory practice.

The specificity of polynucleotide hybridization reactions, together with the extraordinary sensitivity afforded by nucleic acid amplification techniques, has made molecular diagnostics the method of choice for detecting and identifying microbes that are available in only very small quantities. Commonly used DNA probe hybridization formats include: solid phase hybridization, solution-phase hybridization and in situ hybridization. In solid phase hybridization methods, a sample containing microbial polynucleotides is immobilized to a solid support, denatured and then probed with a polynucleotide probe that harbors a detectable label. Unhybridized probe is removed from the system and specifically hybridized probe detected, for example, by autoradiography or direct visual observation. In solution-phase hybridization procedures, the target polynucleotide and the labeled probe are free to interact in an aqueous hybridization buffer. Specifically hybridized probe is then detected as an indicator of the presence of target polynucleotides in the mixture. In situ hybridization using formalin-fixed tissue sections is used for obtaining information about the physical distribution and abundance of microorganisms.

One example of an organism for which a number of polynucleotide-based assays have been described is *Staphylococcus aureus*. For example, Milliman in U.S. Pat. No. 5,292,874 describes a hybridization-based assay to distinguish *S. aureus* from other *Staphylococcus* spp. which employs probes specific for 23S rRNA. The detection of *S. aureus* in biological samples is important as within the genus *Staphylococcus, S. aureus* is the most clinically significant species due to the incidence and severity of the infections it can cause (Morse, Staphylococci, in *Medical Microbiology and Infectious Diseases,* Abraham Braude, editor, W. B. Saunders Company, Philadelphia, Pa., 1981). Moreover, *S. aureus* is a prominent agent of nosocomial infections, and methicillin resistant strains (MRSA) have emerged as a major epidemiological problem in hospitals throughout the United States.

Vancomycin resistant enterococci (VRE) represent another emerging class of drug resistant bacteria. Since these organisms were first identified in 1986, nearly 30 years after vancomycin was clinically introduced, it has been established that vancomycin resistance is primarily conferred by either of two functionally similar operons, VanA and VanB. These operons, transfer of which can be mediated by plasmids or transposons, are complex resistance determinants that may have evolved in other species and then been acquired by enterococci. Frequently identified risk factors for VRE colonization and infection include prolonged hospital stays, exposure to intensive care units, transplants, hematologic malignancies, and exposure to antibiotics. Notably, more than 95% of VRE recovered in the United States are *Enterococcus faecium*, and virtually all are resistant to high levels of ampicillin. (Rice, L., *Emerging Infectious Diseases* 7:183 (2001))

Because vancomycin resistance is transferrable by genetic means, there is the possibility that resistance to this important antibiotic can be acquired by other microorganisms, such as *Staphylococcus aureus*. Indeed, conjugative transfer of the VanA gene from *Enterococcus faecalis* to *S. aureus* has already been demonstrated in vitro. It has been speculated that such a transfer mechanism may underlie the appearance of vancomycin resistant *S. aureus* (VRSA). (Noble et al., *FEMS Microbiol Lett* 93:195 (1992)) Conceivably, there could emerge a strain of *S. aureus* which has acquired resistance to both methicillin and vancomycin (MVSA).

Accordingly, there is a continuing need for the rapid processing of clinical or biological samples, and for the rapid and accurate detection of pathogens and antibiotic resistance genes in clinical samples.

SUMMARY OF THE INVENTION

A first aspect of the invention relates to a device for detecting nucleic acids encoding resistance to an antibiotic. The invented device includes a solid support and a plurality of detectably labeled hybridization probes distributed among a plurality of loci on the solid support. The plurality of loci include a first locus that includes one or more probes that collectively hybridize to ribosomal nucleic acids from a plurality of species of bacteria in the genus *Staphylococcus*, including *Staphylococcus aureus* and *Staphylococcus epidermidis*, but do not hybridize to ribosomal nucleic acids of bacteria in the genus *Enterococcus*. The device further includes a second locus that has one or more probes that collectively hybridize to ribosomal nucleic acids from a plurality of bacteria in the genus *Enterococcus*, including *Enterococcus faecalis* and *Enterococcus faecium*, but that do not hybridize to *Staphylococcus aureus* or any other bacteria in the genus *Staphylococcus*. The second locus also has at least one probe that hybridizes to ribosomal nucleic acids from *Staphylococcus aureus* but not from other species in the genus *Staphylococcus* or bacteria in the genus *Enterococcus*. The device further includes a third locus having at least one probe that hybridizes to mecA nucleic acids. The device further includes a fourth locus that has one or more probes that collectively hybridize to VanA nucleic acids and to VanB nucleic acids. In one embodiment of the invention, each of the plurality of detectably labeled hybridization probes is a detectably labeled soluble hybridization probe. In another embodiment, each of the detectably labeled hybridization probes is labeled with a homogeneously detectable label. For example, the homogeneously detectable label may be a chemiluminescent label. In yet another embodiment, the invented device further includes a fifth locus that includes one or more probes that collectively hybridize to ribosomal nucleic acids from a plurality of species of Grain-positive bacteria (including the high(G+C)subset of Gram-positive bacteria), a plurality of species of bacteria in the family Enterobacteriaceae, a plurality of species of bacteria in the genus *Enterococcus*, and a plurality of species of bacteria in the genus *Staphylococcus*. In still yet another embodiment, the probes that collectively hybridize to VanA nucleic acids and to VanB nucleic acids include at least one probe that hybridizes to VanA nucleic acids and at least one probe that hybridizes to VanB nucleic acids. In a different embodiment, the probes that collectively hybridize to VanA nucleic acids and to VanB nucleic acids include a single probe that hybridizes both to VanA nucleic acids and VanB nucleic acids.

A second aspect of the invention also relates to a device for detecting nucleic acids encoding resistance to an antibiotic. The invented device includes a solid support and a plurality of detectably labeled hybridization probes distributed among a plurality of loci on the solid support. The plurality of loci includes a first locus having one or more probes that collectively hybridize to ribosomal nucleic acids from a plurality of species of bacteria in the genus *Staphylococcus*, including *Staphylococcus aureus* and *Staphylococcus epidermidis*. The device further includes a second locus having a probe that hybridizes to ribosomal nucleic acids from *Staphylococcus aureus* but not other species in the genus *Staphylococcus*. The device further includes a third locus that comprises at least one probe that hybridizes to mecA nucleic acids. The device further includes a fourth locus that has one or more probes that collectively hybridize to ribosomal nucleic acids from a plurality of species of Gram-positive bacteria (including the high(G+C)subset of Gram-positive bacteria), a plurality of species of bacteria in the family Enterobacteriaceae, a plurality of species of bacteria in the genus *Enterococcus*, and a plurality of species of bacteria in the genus *Staphylococcus*. In one embodiment of the invention, the fourth locus includes a pan-bacterial probe having a base sequence that is either SEQ ID NO:16 or SEQ ID NO:19. In a preferred embodiment, the probes of the third locus have base sequences that are any of SEQ ID NO:2, SEQ ID NO:3 or SEQ ID NO:5.

A third aspect of the invention also relates to a device for detecting nucleic acids encoding resistance to an antibiotic. The invented device includes a solid support and a plurality of detectably labeled hybridization probes distributed among a plurality of loci on the solid support. The plurality of loci include a first locus having one or more probes that collectively hybridize to ribosomal nucleic acids from a plurality of bacteria in the genus *Enterococcus*, including *Enterococcus faecalis* and *Enterococcus faecium*. The device further includes a second locus having one or more probes that collectively hybridize to VanA nucleic acids and to VanB nucleic acids. The device further includes a third locus having one or more probes that collectively hybridize to ribosomal nucleic acids from a plurality of species of Gram-positive bacteria (including the high(G+C)subset of Gram-positive bacteria), a plurality of species of bacteria in the family Enterobacteriaceae, a plurality of species of bacteria in the genus *Enterococcus*, and a plurality of species of bacteria in the genus *Staphylococcus*. In one embodiment of the invention, the third locus includes a pan-bacterial probe having a base sequence that is either SEQ ID NO:16 or SEQ ID NO:19. In a preferred embodiment, the probes of the second locus have sequences selected from the group consisting of SEQ ID NO:27, SEQ ID NO:28 and SEQ ID NO:29. In another preferred embodiment, the probes of the second locus have sequences selected from the group consisting of SEQ ID NO:30, SEQ ID NO:40 and SEQ ID NO:41.

A fourth aspect of the invention relates to a method of detecting the presence of a target DNA sequence in a sample containing cells. The invented method includes a step for lysing cells contained in the sample to yield a lysate. There also is included a step for treating the lysate with a basic composition to yield a basic mixture. This is followed by introducing one or more reagents to the basic mixture to yield a reaction mixture at a pH in the range of 4.5-5.5. Next, there is a step for hybridizing the reaction mixture under high stringency hybridization conditions with an oligonucleotide probe to form a hybrid between the oligonucleotide probe and the target DNA. Finally, there is a step for detecting the hybrid as an indicator of the presence of the target DNA sequence. In one embodiment of the invented method, the oligonucleotide probe in the hybridizing step is complementary either to a mecA gene sequence, a VanA gene sequence or a VanB gene sequence. In a different embodiment, the treating step involves heating the basic mixture at a temperature up to 100° C. for a time sufficient to substantially hydrolyze RNA that may be present in the lysate.

A fifth aspect of the invention relates to a probe mix for hybridizing mecA nucleic acids. The invented probe mix includes a first detectably labeled hybridization probe having the sequence of SEQ ID NO:2, a second detectably labeled hybridization probe having the sequence of SEQ ID NO:3, and a third detectably labeled hybridization probe having the sequence of SEQ ID NO:5. More preferably, the first detectably labeled hybridization probe has the length and sequence of SEQ ID NO:2 or the complement thereof, and optionally a non-complementary sequence that does not hybridize to the nucleic acids of the mecA gene; the second detectably labeled hybridization probe has the length and sequence of SEQ ID NO:3 or the complement thereof, and optionally a non-complementary sequence that does not hybridize to the nucleic acids of the mecA gene; and the third detectably labeled hybridization probe has the length and sequence of SEQ ID NO:5 or the complement thereof, and optionally a non-complementary sequence that does not hybridize to the nucleic acids of the mecA gene.

A sixth aspect of the invention relates to a probe mix for detecting VanA nucleic acids. The invented probe mix includes a first detectably labeled hybridization probe having the sequence of SEQ ID NO:27 or the complement thereof; a second detectably labeled hybridization probe having the sequence of SEQ ID NO:28 or the complement thereof; and a third detectably labeled hybridization probe having the sequence of SEQ ID NO:29 or the complement thereof. More preferably, the first detectably labeled hybridization probe has the length and sequence of SEQ ID NO:27 or the complement thereof, and optionally a non-complementary sequence that does not hybridize to the nucleic acids of the VanA gene; the second detectably labeled hybridization probe has the length and sequence of SEQ ID NO:28 or the complement thereof, and optionally a non-complementary sequence that does not hybridize to the nucleic acids of the VanA gene; and the third detectably labeled hybridization probe has the length and sequence of SEQ ID NO:29 or the complement thereof, and optionally a non-complementary sequence that does not hybridize to the nucleic acids of the VanA gene.

A seventh aspect of the invention relates to a probe mix for detecting VanB nucleic acids. The invented probe mix includes a first detectably labeled hybridization probe having the sequence of SEQ ID NO:30 or the complement thereof; a second detectably labeled hybridization probe having the sequence of SEQ ID NO:40 or the complement thereof; and a third detectably labeled hybridization probe having the sequence of SEQ ID NO:41 or the complement thereof. More preferably, the first detectably labeled hybridization probe has the length and sequence of SEQ ID NO:30 or the complement thereof, and optionally a non-complementary sequence that does not hybridize to the nucleic acids of the VanB gene; the second detectably labeled hybridization probe has the length and sequence of SEQ ID NO:40 or the complement thereof, and optionally a non-complementary sequence that does not hybridize to the nucleic acids of the VanB gene; and the third detectably labeled hybridization probe has the length and sequence of SEQ ID NO:41 or the complement thereof, and optionally a non-complementary sequence that does not hybridize to the nucleic acids of the VanB gene.

DETAILED DESCRIPTION OF THE INVENTION

Definitions

As used herein, the following terms have the given meanings unless expressly stated to the contrary.

"Ribosomal nucleic acids" are rRNA and the rDNA that encodes the rRNA.

A "locus" is a place in which something is situated. A locus can be a reaction tube; a single well for containing soluble polynucleotides in a multi-well plate; a single spot of immobilized polynucleotides on a piece of nitrocellulose membrane or a dipstick; or a single spot of immobilized polynucleotides on a "DNA chip." Probe molecules disposed at one locus in a testing device do not mingle with probe molecules disposed at another locus in the device.

An "address" refers to one or more polynucleotide probes at a single locus in a testing device, whereby a hybridization result at the address provides discrete information about the presence or absence of complementary polynucleotide sequences among a collection of polynucleotides undergoing testing. For example, an address may provide information about the presence of rRNA that is of bacterial origin or the presence of one or more specific genes, such as a gene encoding a drug resistance phenotype. Such information could be derived from a single probe or a cocktail of probes disposed at a single locus on a testing device. An address also may provide information about the presence of rRNA from one or more species of microorganism, such as any of *E. coli, S. aureus, C. albicans, P. aeruginosa* and *S. pneumoniae*. For convenience, an address that detects nucleic acids of a particular organism or type of organism is referred to by the name or type of that organism. Thus, a positive hybridization signal at a "pan-bacterial" address would indicate the presence of ribosomal nucleic acids that are of bacterial origin.

A probe "matrix" is a collection of addresses useful for identifying an unknown microorganism, for narrowing the range of possible identities of an unknown organism, and/or the presence of one or more specific genes, in an organism. Probes of the matrix are ordinarily disposed (either by containment of soluble probes or by physical immobilization) at a plurality of physical loci in a testing device where each locus specifically hybridizes nucleic acids from one or a plurality of microorganism species.

A "nucleotide" is a subunit of a nucleic acid conventionally comprising a purine or pyrimidine base, a 5-carbon sugar and a phosphate group. The 5-carbon sugar found in RNA is ribose. In DNA, the 5-carbon sugar is 2'-deoxyribose. The term also includes analogs of such subunits, such as a methoxy group at the 2' position of ribose.

A "non-nucleotide unit" is a unit which does not significantly participate in hybridization of a polymer. Such units must not, for example, participate in any significant hydrogen bonding with a nucleotide, and would exclude units having as a component one of the five nucleotide bases or analogs thereof.

An "oligonucleotide" is a polynucleotide having two or more nucleotide subunits covalently joined together. Oligonucleotides are generally about 10 to about 100 nucleotides in length, or more preferably 10 to 50 nucleotides in length. The sugar groups of the nucleotide subunits may be ribose, deoxyribose, or modified derivatives or analogs thereof such as 2'-O-methyl ribose (referred to herein alternatively as "2'-O-Me", "2' methoxy", "2'-MeO"). The nucleotide subunits may be joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention. Ordinarily, oligonucleotides will be synthesized by organic chemical methods and will be single-stranded unless specified otherwise. Oligonucleotides can be labeled with a detectable label.

A "target nucleic acid" is a nucleic acid comprising a target nucleic acid sequence.

A "target nucleic acid sequence," "target nucleotide sequence" or "target sequence" is a specific deoxyribonucleotide or ribonucleotide sequence that can be hybridized by an oligonucleotide. For instance, a "target nucleic acid sequence region" of bacteria in the *Staphylococcus genus* refers to a nucleic acid sequence present in nucleic acid or a sequence complementary thereto found in Staphylococcal bacteria, which is not present in nucleic acids of other species. Nucleic acids having nucleotide sequences complementary to a target sequence may be generated by target amplification techniques such as polymerase chain reaction (PCR) or transcription mediated amplification (e.g., see U.S. Pat. No. 5,824,518).

A "probe" is a single-stranded polynucleotide that combines with a complementary single-stranded target polynucleotide to form a double-stranded hybrid. A probe may be an oligonucleotide or a nucleotide polymer, and may contain a detectable moiety which can be attached to the end(s) of the probe or can be internal to the sequence of the probe. The nucleotides which combine with the target polynucleotide need not be strictly contiguous as may be the case with a detectable moiety internal to the sequence of the probe.

A "pan-bacterial" probe is capable of forming double-stranded hybrids with complementary sequences that are found in the ribosomal nucleic acids of a plurality of species of bacteria. For example, a pan-bacterial probe can specifically hybridize to ribosomal nucleic acids from a plurality of species of Gram-positive bacteria (including the high(G+C) subset of Gram-positive bacteria known as the "Actinomycetes"), a plurality of species of bacteria in the family Enterobacteriaceae, a plurality of species of bacteria in the genus *Enterococcus*, and a plurality of species of bacteria in the genus *Staphylococcus*. A pan-bacterial probe does not hybridize to the nucleic acids of fungal organisms.

A "detectable moiety" is a label molecule attached to, or synthesized as part of, a polynucleotide probe. This molecule should be uniquely detectable and will allow the probe to be detected as a result. These detectable moieties include but are not limited to radioisotopes, colorimetric, fluorometric or chemiluminescent molecules, enzymes, haptens, redox-active electron transfer moieties such as transition metal complexes, metal labels such as silver or gold particles, or even unique oligonucleotide sequences.

A "hybrid" is the complex formed between two single-stranded polynucleotide sequences by Watson-Crick base pairings or non-canonical base pairings between the complementary bases. By "nucleic acid hybrid" or "probe:target duplex" is meant a structure that is a double-stranded, hydrogen-bonded structure, preferably 10 to 100 nucleotides in length, more preferably 14 to 50 nucleotides in length. The structure is sufficiently stable to be detected by means such as chemiluminescent or fluorescent light detection, colorimetry, autoradiography, electrochemical analysis or gel electrophoresis. Such hybrids include RNA:RNA, RNA:DNA, or DNA:DNA duplex molecules.

"Hybridization" is the process by which two complementary strands of polynucleotide combine to form a stable double-stranded structure ("hybrid").

"Stable" means substantially resistant to chemical or biochemical degradation, reaction, decomposition, displacement or modification.

"Stability" means the resistance of a substance to chemical or biochemical degradation, reaction, decomposition, displacement or modification.

The term "stringency" is used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two polynucleotide strands forming a hybrid. Stringency conditions are chosen to maximize the difference in stability between the hybrid formed with the target and the non-target polynucleotide.

The term "probe specificity" refers to a characteristic of a probe which describes its ability to distinguish between target and non-target sequences. Probe specificity is dependent on sequence and assay conditions and may be absolute (i.e., the probe can distinguish between target organisms and any non-target organisms), or it may be functional (i.e., the probe can distinguish between the target organism and any other organism normally present in a particular sample). Many probe sequences can be used for either broad or narrow specificity determinations depending on the conditions of use.

"Polynucleotide" means either RNA or DNA, along with any synthetic nucleotide analogs or other molecules that may be present in the sequence and that do not prevent hybridization of the polynucleotide with a second molecule having a complementary sequence. The term includes polymers containing analogs of naturally occurring nucleotides and particularly includes analogs having a methoxy group at the 2' position of the ribose (MeO).

A "helper oligonucleotide" is an oligonucleotide that binds a region of a target polynucleotide other than the region that is bound by an assay probe. These oligonucleotides impose new secondary and tertiary structures on the targeted region of the single-stranded polynucleotide so that the rate of binding of the assay probe is accelerated. Although helper oligonucleotides are not labeled with a detectable label, they facilitate binding of labeled probes and so indirectly enhance hybridization signals.

A "biological sample" refers to a sample of material that is to be tested for the presence of microorganisms or nucleic acid thereof. The biological sample can be obtained from an organism such as a human patient, a laboratory mammal such as a mouse, rat, pig, monkey or other member of the primate family, by drawing a blood sample, sputum sample, spinal fluid sample, a urine sample, a nasal swab or a throat swab, or a culture of such a sample. Ordinarily, the biological sample will contain hybridizable polynucleotides. These polynucleotides may have been released from organisms that comprise the biological sample, or alternatively can be released from the organisms in the sample using techniques such as sonic disruption or enzymatic or chemical lysis of cells to release polynucleotides so that they are available for hybridization with a polynucleotide probe.

As used herein "acridinium ester" means any of the family of chemiluminescent compounds based on the acridinium ring structure having an ester linkage at the C-9 position.

An "analyte" means any substance capable of undergoing a binding reaction with one or more specific binding partners, including, without limitation, antigens and antibodies thereto, haptens and antibodies thereto; hormones, drugs, metabolites, vitamins, coenzymes and their binding partners, including receptors; polynucleotides, oligonucleotides, and hybrids of polynucleotides or oligonucleotides and antibodies and binding substances thereto; polynucleotides or oligonucleotides and hybridizable polynucleotides or oligonucleotides thereto; metals and chelating agents thereto.

A "binding partner" means any molecule or substance capable of undergoing a specific binding reaction with an analyte.

"Bound" means a condition in which a binding interaction has been formed between a molecule and its specific binding partner.

"$T_m$" refers to the temperature at which 50% of the probe is converted from the hybridized to the unhybridized form.

One skilled in the art will understand that probes that substantially correspond to a reference sequence or region can vary from that reference sequence or region and still hybridize to the same target nucleic acid sequence. Probes of the present invention substantially correspond to a nucleic acid sequence or region if the percentage of identical bases or the percentage of perfectly complementary bases between the probe and its target sequence is from 100% to 80% or from 0 base mismatches in a 10 nucleotide target sequence to 2 bases mismatched in a 10 nucleotide target sequence. In preferred embodiments, the percentage is from 100% to 85%. In more preferred embodiments this percentage is from 90% to 100%; in other preferred embodiments, this percentage is from 95% to 100%. Probes that substantially correspond to a reference sequence or region include probes having any additions or deletions which do not prevent the probe from having its claimed property, such as being able to preferentially hybridize under high stringency hybridization conditions to its target nucleic acid over non-target nucleic acids.

By "sufficiently complementary" or "substantially complementary" is meant nucleic acids having a sufficient amount of contiguous complementary nucleotides to form, under high stringency hybridization conditions, a hybrid that is stable for detection.

By "antisense" is meant a nucleic acid molecule perfectly complementary to a reference (i.e., sense) nucleic acid molecule.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

Introduction to the Invention

The present invention relates to polynucleotide-based methods, compositions, kits and devices that can be used for detecting the nucleic acids that encode resistance to methicillin and/or vancomycin. More specifically, the invention provides for detection of the mecA gene, which is associated with methicillin-resistance of microorganisms, as well as for detection of the VanA and VanB genes, which are associated with vancomycin resistance of microorganisms. The present invention also relates to a rapid method for processing biological samples to obtain DNA, preferably which is substantially free of RNA, including ribosomal RNA (rRNA).

As described hereinbelow, a rapid sample processing method is provided which results in a sample that has denatured DNA and preferably is substantially free of rRNA. The method includes providing a sample, for instance, a cellular lysate which contains at least partially denatured DNA. In one embodiment, cells are treated with a lysing agent and then heat. In another embodiment, cells are treated with a lysing agent and heat simultaneously. The sample is then treated with a base and optionally heat to substantially decrease or eliminate RNA, including rRNA, in the sample. As used herein, a "substantial decrease" in rRNA in a sample means a decrease of at least 100-fold, preferably at least 500-fold, and more preferably at least 900-fold or more, relative to an untreated (control) sample. After base hydrolysis, the sample is treated with one or more reagents to yield a reaction mixture at a pH of about 4.5 to about 5.5, as well as reagents in an amount which results in a reaction mixture suitable for hybridizing polynucleotides (i.e., a mixture effective for a hybridization reaction with one or more probes and a target polynucleotide). While base treatment alone yielded reliable results, the combination of thermal and base denaturation yielded enhanced results. More specifically, the combination yielded enhanced rRNA degradation and denaturation of double-stranded DNA. Moreover, the combination of thermal and base denaturation resulted in reduced background signals and higher probe-specific signals relative to base denaturation alone. Further, if a probe in a hybridization reaction can bind to both RNA and DNA targets, the decrease in RNA in the sample reduces the level of RNA target relative to a genomic DNA target. In this way, a rDNA target can be used as an internal control and/or organism identifier in a hybridization reaction.

The above-described sample processing method was employed to identify an isolate as a member of the *Staphylococcus* genus, and more specifically as *S. aureus*, coupled with the determination of its mecA status, in one hour. Indeed, 290 clinical and 24 ATCC isolates representing 303 *S. aureus* and 11 other *Staphylococcus* spp. were processed and hybridized with mecA gene probes in a hybridization protection assay (HPA). Results of the mecA HPA assay were compared to oxacillin (Ox) minimum inhibitory concentrations (MICs). Using the mecA probes disclosed herein, there was 100% correlation with 263 methicillin resistant *S. aureus* (MRSA) and methicillin sensitive *S. aureus* (MSSA). Additionally, 15 of 27 borderline resistant *S. aureus* (BORSA) were positive by the hybridization assay. mecA PCR and a latex agglutination assay (Oxoid, UK) results on the borderline isolates demonstrated 100% agreement with the probe results. Thus, by probing a sample with a ribosomal DNA probe and DNA probes specific for multiple regions within the mecA gene, a single processed sample yielded both isolate identification and antibiotic marker detection. This multi-probe system also serves as an internal control, as rDNA copy number is quite stable for a given organism, and so ensures that adequate target DNA is present to provide meaningful results. This advantageously can eliminate false-negative results. In one embodiment, testing for methicillin resistance status may be performed after a primary blood culture bottle turns positive, thereby eliminating the need for plating and incubating samples.

The invented method can lead to the appropriate choice of antibiotics to treat an infection, thereby reducing the occurrence of antibiotic resistance. This rapid probe-based assay allows the simultaneous identification and mecA gene detection of *Staphylococcus* directly from plates, and so is very useful in clinical laboratories and hospitals to identify MRSA and methicillin-resistant, coagulase-negative Staphylococci (MRCoNS). Moreover, it is even possible to perform simultaneous testing for methicillin-resistance and vancomycin-resistance, as described below.

Thus, one embodiment of the invention includes a method for detecting the mecA gene in a sample. The method includes lysing a sample comprising cells and treating the lysate with a basic composition in an amount and under conditions effective to substantially decrease or eliminate RNA in the sample, yielding a basic mixture. In one embodiment, the sample does not contain in vitro amplified nucleic acids. To denature the DNA in the sample, the sample may be treated with heat at a temperature of at least 95° C. for at least 5 minutes, concurrent with, or subsequent to, addition of a lysing reagent. Alternatively, DNA in a sample may be denatured by treatment with a basic composition, optionally with concurrent heat treatment, for example at 60° C. Preferably, the DNA in the sample is treated with heat, for example at a temperature of at least 95° C., concurrent with, or subsequent to, addition of a lysing reagent followed by treatment with a basic composition, as the combination of treatments was found to improve the sensitivity of target DNA detection. In one embodiment, the basic composition includes a hydroxide solution. The hydrolyzed sample is then contacted with one or more reagents in an amount that alters the pH of the basic mixture to a pH of about 4.0 to about 6.0, preferably a pH of about 4.5 to about 5.5, and result in a buffered mixture suitable for conducting a hybridization reaction. In one embodiment, the one or more reagents added to alter the pH of the basic mixture include an acid, such as HCl, and optionally a buffering compound, e.g., a succinate salt. In one embodiment, the basic mixture is aliquoted into separate reaction vessels, each aliquot then contacted with one or more reagents in an amount that alters the pH of the basic mixture to a pH of about 4.0 to about 6.0 and results in a buffered hybridization reaction mixture. Each buffered hybridization reaction mixture can be contacted with at least one probe, such as a probe specific for mecA sequences or either or both of the VanA and VanB sequences, under conditions, preferably, high stringency conditions, effective to hybridize the probe to denatured target DNA. Optionally, at least one buffered hybridization reaction mixture is contacted with one or more probes that are different from the probe(s) in other hybridization reaction mixtures. In another embodiment, the basic mixture is contacted with one or more reagents in an amount that alters the pH of the basic mixture to a pH of about 4.0 to 6.0 and results in a buffered mixture suitable for conducting a hybridization reaction, and the buffered hybridization reaction mixture, or a portion thereof, is further contacted with at least one probe under conditions, preferably, high stringency conditions, effective to hybridize the probe to denatured target DNA. For instance, a portion of the hybridization reaction mixture may be added to a reaction vessel and one or more probes added to the vessel. Alternatively, a portion of the hybridization reaction mixture may be added to at least two reaction vessels and different probes added to each of those vessels. Alternatively, the hybridization reaction mixture or a portion thereof is added to one or more probes in a reaction vessel. Exemplary high stringency conditions include a hybridization reaction mixture including 0.48 M sodium phosphate buffer, 0.1% sodium dodecyl sulfate and 1 mM each of EDTA and EGTA, or including 0.6 M LiCl, 1% lithium lauryl sulfate, 50 to 60 mM lithium succinate and 10 mM each EDTA and EGTA, and temperatures of at least 50° C.

In one preferred embodiment, the one or more probes used in the hybridization reaction includes a detectable moiety. Optionally, after the hybridization reaction is subjected to conditions effective to result in hybrid formation, the hybridization reaction is subjected to conditions effective to decrease or eliminate the amount of unhybridized probe. Then the presence or amount of hybridized probe is detected or determined. Although the sample processing method described herein was employed to prepare samples to detect mecA DNA, the sample processing method may be employed to prepare a sample to detect any DNA target sequence.

The invention also provides a method for detecting mecA sequences in a sample. The method comprises contacting a sample comprising denatured DNA with one or more mecA oligonucleotide probes under high stringency hybridization conditions effective to form a hybrid between the oligonucleotide probes and mecA DNA. The presence of hybrid formation is detected or determined thereafter. The probes include sequences substantially corresponding to nucleotides 304 to 338 of the mecA gene, the complement thereof, or a portion thereof, sequences substantially correspond to nucleotides 501 to 531 of the mecA gene, the complement thereof, or a portion thereof, or sequences substantially correspond to nucleotides 1010 to 1044 of the mecA gene, the complement thereof, or a portion thereof. Preferably, the probes are labeled, for example with a chemiluminescent label, a fluorescent label or a radioactive label. In one embodiment, at least three mecA oligonucleotide probes are employed to detect or determine the mecA status of a sample. In one preferred embodiment, at least one probe has at least one nucleotide that has a substituted ribose moiety, such as a methoxy group at the 2' position of the ribose moiety.

Optionally, one or more non-mecA gene probes, such as a probe specific for ribosomal nucleic acids, may be employed in addition to the mecA gene probes to identify the microorganism in the sample and/or to confirm that sufficient DNA was present in the sample to permit detection of the mecA gene (i.e., an internal control). For instance, a rDNA probe specific for one or more organisms, such as a probe specific for *Staphylococcus* bacteria, may be used to identify the organism in the sample. In one embodiment, the sample processing method described herein is employed to prepare the sample prior to detecting or determining the mecA status of the sample. Although the mecA gene is generally associated with *S. aureus*, other Staphylococcal species (coagulase-negative Staphylococci, "CoNS") may contain the mecA gene as the result of lateral transfer of genetic information between the microorganisms. Therefore, an identification or internal control reaction used in conjunction with a mecA reaction may employ a rRNA or rDNA probe for an organism other than *S. aureus*. Thus, in one embodiment, the method includes comparing the presence or amount of hybrid formation in a sample contacted with mecA gene probes to the presence or amount of hybrid formation in a corresponding sample contacted with a probe specific for rRNA or rDNA.

In another embodiment of the invention, one or more mecA gene probes are employed with a sample which contains amplified nucleic acid. The method includes contacting a sample comprising amplified mecA nucleic acid, with at least one mecA oligonucleotide probe under high stringency hybridization conditions effective to form a hybrid between the probe and the amplified mecA nucleic acid. In one embodiment, the amplified nucleic acid is RNA amplified using transcription mediated amplification. Optionally, prior to amplification, a cellular sample is contacted with methicillin to induce transcription from the mecA gene. Then the presence or amount of hybrid formation is detected or determined. Probes useful in this embodiment of the invention includes those with sequences substantially corresponding to nucleotides 304 to 338 of the mecA gene, the complement thereof, or a portion thereof, nucleotides 501 to 531 of the mecA gene, the complement thereof, or a portion thereof, or nucleotides 1010 to 1044 of the mecA gene, the complement thereof, or a portion thereof.

The invention also includes a probe mix. The mix includes two or more of a first oligonucleotide substantially corresponding to nucleotides 304 to 338 of the mecA gene, the complement thereof, or a portion thereof, a second oligonucleotide substantially corresponding to nucleotides 501 to 531 of the mecA gene, the complement thereof, or a portion thereof, and a third oligonucleotide substantially corresponding to nucleotides 1010 to 1044 of the mecA gene, the complement thereof, or a portion thereof. Each oligonucleotide in the mix hybridizes under stringent hybridization conditions to mecA genomic DNA. In one embodiment, the mix includes a first oligonucleotide corresponding to nucleotides 304 to 338 of the mecA gene, a second oligonucleotide corresponding to the complement of nucleotides 501 to 531 of the mecA gene, and a third oligonucleotide corresponding to nucleotides 1010 to 1044 of the mecA gene. In another embodiment, the mix includes a first oligonucleotide corresponding to nucleotides 304 to 338 of mecA, a second oligonucleotide corresponding to the complement of nucleotides 501 to 531 of the mecA gene, and a third oligonucleotide corresponding to the complement of nucleotides 1010 to 1044 of the mecA gene. In another embodiment, the mix includes a first oligonucleotide corresponding to the complement of nucleotides 304 to 338 of mecA, a second oligonucleotide corresponding to the complement of nucleotides 501 to 531 of the mecA gene, and a third oligonucleotide corresponding to nucleotides 1010 to 1044 of the mecA gene. In yet another embodiment, the mix includes a first oligonucleotide corresponding to nucleotides 304 to 338 of the mecA gene, a second oligonucleotide corresponding to nucleotides 501 to 531 of the mecA gene, and a third oligonucleotide corresponding to the complement of nucleotides 1010 to 1044 of the mecA gene. Preferably, at least one oligonucleotide in the mix comprises one or more nucleotide analogs comprising a 2'-O-methyl ribosyl analog rather than a ribosyl or deoxyribosyl moiety.

The invention further includes a kit with probes useful for detecting the mecA gene in a test sample. The kit includes one or more of a first oligonucleotide comprising sequences corresponding to nucleotides 304 to 338 of the mecA gene, the complement thereof, or a portion thereof, a second oligonucleotide comprising sequences corresponding to nucleotides 501 to 531 of the mecA gene, the complement thereof, or a portion thereof, and a third oligonucleotide comprising sequences corresponding to nucleotides 1010 to 1044 of the mecA gene, the complement thereof, or a portion thereof, wherein each oligonucleotide hybridizes under stringent hybridization conditions to mecA genomic DNA. The kit optionally includes probes useful for detecting single-copy genes other than mecA, including other drug resistance genes, or to detect multiple copy genes, such as rDNA genes.

The invention thus provides for the use of two or more probes, one of which is optionally employed as an identifier probe capable of providing information about the identity of an organism. For example, the identifier probe may be capable of providing information about the group, family, genus or species of an organism. Alternatively, an identifier probe may be chosen to distinguish Gram-positive and Gram-negative bacteria, or to make a species- or strain-level identification. More preferably, the use of a "matrix" of polynucleotide hybridization probes could be used in conjunction with the antibiotic resistance probes described herein. In one embodiment, certain hybridization probes are specific for a selected gene, such as the mecA gene, while other hybridization probes are specific for nucleic acids, such as rRNA and rDNA, of various species or taxonomically related groups of organisms. Using these probes, it is possible to determine the status of the organism, meaning whether the genome of the organism includes the gene or sequences related to the gene, and the species of the organism. The method is particularly suited for use in connection with automated systems.

Even negative results in a probe matrix hybridization procedure can be meaningful when taken in the context of other results from the matrix. For example, if it is determined from a two-locus matrix that a sample contains polynucleotides that give a positive hybridization signal at a first address that identifies *S. aureus*, and negative results at a second address that identifies the mecA gene, then the combination of results would indicate that the polynucleotides were derived from a *S. aureus* that is mecA-negative (mecA(−)). Alternatively, if it is determined from a two-locus matrix that a sample does not contain polynucleotides that hybridize at a first address that identifies nucleic acids of bacteria that are members of the *Staphylococcus* genus (i.e., a negative result at a *Staphylococcus* genus address) and a positive result at a second address that identifies the mecA gene, then the combination of results would indicate that the polynucleotides were derived from a non-*Staphylococcus* organism that is mecA-positive (mecA(+)).

Another aspect of a matrix-based method of gene and/or microbe identification relates to the use of a combination of probes in a single hybridization reaction, such as may be conducted in a single well of a multi-well plate. In one embodiment, a combination of polynucleotide probes that hybridize to a selected gene, for instance, the mecA gene, is employed with one or more probes for another gene, e.g., rDNA genes, which optionally may be employed as an internal control. In a preferred embodiment, probes for the mecA gene are labeled with a label that is different from the label on the internal control probe. This arrangement facilitates detection of both targets in a single hybridization reaction. In another preferred embodiment, the probes for detecting the mecA gene and the probes that are specific for ribosomal nucleic acids are labeled with the same detectable label, or with labels that are not distinguished from each other during a detection step which is used in a method employing the invented apparatus or device.

I. Probe Selection and Preparation

It is not always necessary to determine the entire nucleic acid sequence of a gene of interest in order to obtain a probe specific for that gene. In a highly preferred embodiment, all of the probes are particularly selected for use under a single set of hybridization conditions, including a single temperature and/or a single set of ionic strength conditions. The following guidelines are useful for designing probes with desirable characteristics.

First, the stability of the probe:target polynucleotide hybrid is chosen to be compatible with the assay conditions. This may be accomplished by avoiding long A and T rich sequences, by terminating the hybrids with G:C base pairs and by designing the probe in such a way that the $T_m$ will be appropriate for standard conditions to be employed in the assay. The nucleotide sequence of the probe should be chosen so that the length and % G and % C result in a probe having a $T_m$ about 2 to 10° C. higher than the temperature at which the final assay is performed. The base composition of the probe is significant because G:C base pairs exhibit greater thermal stability when compared with A:T base pairs. Thus, hybrids involving complementary polynucleotides having a high G:C content are generally stable at higher temperatures when compared with hybrids having a lower G:C content.

Second, the position at which the probe binds its target polynucleotide is chosen to minimize the stability of hybrids formed between probe:non-target polynucleotides. This may be accomplished by minimizing the length of perfect complementarity with polynucleotides of non-target organisms, by avoiding G:C rich regions of homology with non-target sequences, and by positioning the probe to span as many destabilizing mismatches as possible. Whether a probe sequence is useful for detecting only a specific type of organism or gene depends largely on thermal stability differences between probe:target hybrids and probe:non-target hybrids. The differences in $T_m$ should be as large as possible to produce highly specific probes.

The length of the target polynucleotide sequence and the corresponding length of the probe sequence also are important factors to be considered when designing a probe. While it is possible for polynucleotides that are not perfectly complementary to hybridize to each other, the longest stretch of perfectly homologous base sequence is ordinarily the primary determinant of hybrid stability.

Third, regions which are known to form strong internal structures inhibitory to hybridization of a probe are less preferred as targets. Probes having extensive self-complementarity also should be avoided.

Once a presumptive unique sequence has been identified, corresponding oligonucleotides are produced. Defined oligonucleotides that can be used to practice the invention can be produced by any of several well-known methods, including automated solid-phase chemical synthesis using phosphoramidite precursors (Barone et al., *Nucl. Acids Res.* 12:4051 (1984)). Other well-known methods for construction of synthetic oligonucleotides may, of course, be employed (see Sambrook et al., *Molecular Cloning: A Laboratory Manual*, 11 (1989)). All of the oligonucleotides of the present invention may be modified with chemical groups to enhance their performance. Thus, it is to be understood that references to "oligonucleotide probes" or "helper oligonucleotides" or simply "oligonucleotides" embrace polymers of native nucleotides as well as polymers that include at least one nucleotide analog. Backbone-modified oligonucleotides, such as those having phosphorothioate or methylphosphonate groups, are examples of analogs that can be used in conjunction with oligonucleotides of the present invention. These modifications render the oligonucleotides resistant to the nucleolytic activity of certain polymerases or to nuclease enzymes. Other analogs that can be incorporated into the structures of the oligonucleotides include peptide nucleic acids, or "PNAs." The PNAs are compounds comprising ligands linked to a peptide backbone rather than to a phosphodiester backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker. PNAs are able to bind complementary single-stranded DNA (ssDNA) and RNA strands. Methods for making and using PNAs are disclosed in U.S. Pat. No. 5,539,082. Another type of modification that can be used to make oligonucleotides having the sequences described herein involves the use of non-nucleotide linkers (e.g., see U.S. Pat. No. 6,031,091) between nucleotides in the nucleic acid chain which do not interfere with hybridization or optionally elongation of a primer.

Yet other analogs include those which increase the binding affinity of a probe to a target nucleic acid and/or increase the rate of binding of the probe to the target nucleic acid relative to a probe without the analog. Such analogs include those with a modification (substitution) at the 2' position of a ribofuranosyl nucleotide. When employed in hybridization reactions, probes containing one or more of these analogs, with their resulting changes in hybridization properties, may be shorter in length than corresponding DNA probes. The use of shorter oligonucleotides to specifically bind target nucleic acids at a given temperature has additional advantages. For instance, shorter oligonucleotides will generally have a greater ability to discriminate perfectly complementary targets from "mismatched" base sequence regions. Shorter oligonucleotides are also less likely to overlap undesirable base sequences. The use of higher hybridization temperatures kinetically drives the hybridization reaction, resulting in faster hybridization rates than would occur at lower temperatures. Further, modified oligonucleotides may result in faster hybridization rates than the unmodified versions, even when the temperature is not raised.

Thus, hybridization assay probes and/or helper oligonucleotides can all be designed to contain modified bases which, alone or in combination, may have the advantage of increasing the rate of target-specific hybridization.

Analogs having a modification at the 2' position of the ribose, e.g., an alkyl, and alkoxy or a halide substitution, are one preferred embodiment. In one preferred embodiment, oligonucleotides contain nucleotide analogs having 2'-O-methylribofuranosyl moieties linked to a nitrogenous base. Other substitutions at the 2' position of the sugar are expected to have similar properties so long as the substitution is not so large as to cause steric inhibition of hybridization.

Additionally, other modifications which increase the $T_m$ of a modified oligonucleotide:target hybrid would reasonably be expected to contribute to increases in the rate of hybridization as well. Such modifications may occur at the 2' position (or other positions) of the deoxyribofuranosyl or ribofuranosyl moiety (such as 2' halide substitutions), on the nitrogenous bases (such as N-diisobutylaminomethylidene-5-(1-propynyl)-2'-deoxycytidine; a cytidine analog, or 5-(1-propynyl)-2'-deoxyuridine); a thymidine analog, or in the linkage moiety.

Preferably, probes are labeled. Essentially any labeling and detection system that can be used for monitoring specific nucleic acid hybridization can be used in conjunction with the probes disclosed herein when a labeled probe is desired. Included among the collection of useful labels are: radiolabels, enzymes, haptens, linked oligonucleotides, colorimetric, fluorometric or chemiluminescent molecules, and redox-active moieties that are amenable to electrochemical detection methods. Standard isotopic labels that can be used to produce labeled oligonucleotides include $^3$H, $^{35}$S, $^{32}$P, $^{125}$I, $^{57}$Co and $^{14}$C. When using radiolabeled probes, hybrids can be detected by autoradiography, scintillation counting or gamma counting.

Non-isotopic materials can also be used for labeling oligonucleotide probes. These non-isotopic labels can be positioned internally or at a terminus of the oligonucleotide probe. Modified nucleotides can be incorporated enzymatically or chemically with modifications of the probe being performed during or after probe synthesis, for example, by the use of non-nucleotide linker groups. Non-isotopic labels include colorimetric molecules, fluorescent molecules, chemiluminescent molecules, enzymes, cofactors, enzyme substrates, haptens or other ligands. Acridinium esters are one example of chemiluminescent labels useful for detecting probe hybrids.

Indeed, any number of different non-isotopic labels can be used for preparing labeled oligonucleotides in accordance with the invention. Preferred chemiluminescent molecules include acridinium esters of the type disclosed in U.S. Pat. No. 5,283,174 for use in connection with homogenous protection assays, and of the type disclosed in U.S. Pat. No. 5,656,207 for use in connection with assays that quantify multiple targets in a single reaction. The disclosures of these U.S. patents are hereby incorporated by reference. U.S. Pat. No. 5,998,135 discloses yet another method that can be used for labeling and detecting probes using fluorimetry to detect fluorescence emission from lanthanide metal labels disposed on probes, where the emission from these labels becomes enhanced when it is in close proximity to an energy transfer partner. Preferred electrochemical labeling and detection approaches are disclosed in U.S. Pat. Nos. 5,591,578 and 5,770,369, and PCT/US98/12082, the disclosures of which are hereby incorporated by reference. Redox active moieties useful as electrochemical labels include transition metals such as Cd, Mg, Cu, Co, Pd, Zn, Fe and Ru.

In some applications, probes exhibiting at least some degree of self-complementarity are desirable to facilitate detection of probe:target duplexes in a test sample without first requiring the removal of unhybridized probe prior to detection. By way of example, structures referred to as "molecular torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions (which may be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith. Molecular torches are fully described in U.S. Pat. No. 6,361,945, the disclosure of which is hereby incorporated by reference.

Another example of a self-complementary hybridization assay probe that may be used in conjunction with the invention is a structure commonly referred to as a "molecular beacon." Molecular beacons comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are fully described in U.S. Pat. No. 5,925,517, the disclosure of which is hereby incorporated by reference. Molecular beacons useful for detecting specific nucleic acid sequences may be created by appending to either end of one of the probe sequences disclosed herein, a first nucleic acid arm comprising a fluorophore and a second nucleic acid arm comprising a quencher moiety. In this configuration, the specific probe sequence disclosed herein serves as the target-complementary "loop" portion of the resulting molecular beacon.

Molecular beacons preferably are labeled with an interactive pair of detectable labels. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Highly preferred label moieties for the invented molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the invention, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL and the BLACK HOLE QUENCHER moieties which are available from Biosearch Technologies, Inc., (Novato, Calif.).

Alternative procedures for detecting particular genes can be carried out using either labeled probes or unlabeled probes. For example, hybridization assay methods that do not rely on the use of a labeled probe are disclosed in U.S. Pat. No.

5,945,286 which describes immobilization of unlabeled oligonucleotide probe analogs made of peptide PNAs, and detectably labeled intercalating molecules which can bind double-stranded PNA probe/target nucleic acid duplexes. In these procedures, as well as in certain electrochemical detection procedures, such as those disclosed in PCT/US98/12082, PCT/US98/12430 and PCT/US97/20014, the oligonucleotide probe is not required to harbor a detectable label.

II. Probe Specificity

High stringency conditions useful for conducting the hybridization procedures disclosed herein include conditions of 55° C. to 65° C. when the salt concentration is in the range of 0.6 to 0.9 M. Preferred salts include lithium chloride, but other salts such as sodium chloride and sodium citrate also can be used in the hybridization solution. Other useful high stringency hybridization conditions are alternatively provided by 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA. It is preferred that all of the probes for hybridization at about 60° C. will have $T_m$ values in the range of from 63° C. to about 78° C.

III. Exemplary Methods and Probes of the Invention

Nucleic acid probes specific for a gene of interest, such as a drug resistance gene, optionally in combination with one or more probes specific for a group of organisms find use in an assay for detecting the presence of the gene of interest in a biological sample that includes nucleic acids, and optionally for identifying a group of organisms and/or to serve as an internal control. For instance, a plurality of probes specific for the mecA gene and a probe specific for *Staphylococcus* rRNA or rDNA may be employed to determine whether a biological sample contains mecA(+) or mecA(−) organisms, such as mecA(+) or mecA(−) Staphylococci including mecA(+) or mecA(−) *S. aureus*. Likewise, a plurality of probes specific for the VanA and VanB genes encoding vancomycin resistance and one or more probes specific for the rRNA or rDNA of one or more *Enterococcus* species that include *E. faecalis* and *E. faecium* may be employed to determine whether a biological sample contains vancomycin-resistant *Enterococcus*. Including a probe specific for the rRNA or rDNA of *S. aureus* among the other probes of this latter panel provides a means for rapidly identifying vancomycin-resistant *S. aureus*.

A. Sample Processing Method

Since hybridization signals measured using certain probes intended for detecting DNA targets may actually be due to reactivity with RNA, which may be present in excess relative to the intended DNA target sequence, conditions which resulted in a substantial decrease or elimination of RNA were determined. Cells were lysed with a lysing agent in an amount which released polynucleotides from the cells, thus forming a lysate. Polynucleotides were denatured by heat treatment, for example, by heating at temperatures greater than 90° C., preferably at least 95° C., and more preferably at least 100° C. to 105° C., for at least 5, and preferably at least 10 minutes and optionally 25 minutes or more. The lysing and denaturation steps may be conducted consecutively or simultaneously.

To remove RNA from the lysate, the lysate can be treated with base in an amount and under conditions which result in a substantial decrease in RNA in the sample. Any base may be employed in this regard. In one embodiment, hydroxide is employed to remove RNA from the sample. Preferably, the hydroxide is added to a final concentration of about 0.2 to about 1.0 N and the resulting mixture heated at about 50-60° C. for 5 minutes, and optionally up to 30 minutes or more. The mixture is then neutralized with an acidic composition to achieve a pH in the range of about 4.0-6.0, and reagents added to yield a buffered mixture containing, for example, monovalent ions, detergent, and succinate buffer at a final concentration of about 20 to about 100 mM. The neutralized mixture is suitable for conducting a hybridization reaction.

B1. MecA Probes

MecA sequences and structurally and/or functionally related sequences from a collection of organisms were aligned to identify candidate conserved sequences that could be used to distinguish mecA(+) organisms from mecA(−) organisms. Thus, by examining partial or complete sequences of mecA(+) genes of various organisms including the Staphylococcal organisms, aligning those sequences with structurally and/or functionally related sequences to reveal areas of maximum homology and areas of sequence variation, sequences were identified that are conserved among mecA genes but that exhibit mismatches with structurally and/or functionally related genes. Based on such considerations, the following regions of the mecA gene were selected for testing as probes: nucleotides 304 to 338, nucleotides 501 to 531, and nucleotides 1010 to 1044 of the mecA gene. Such conserved sequences were then tested against a panel of mecA standards and bacterial lysates to verify their utility as probes under laboratory conditions. In particular, probes that preferentially hybridized to a nucleic acid target region to form a detectable duplex were chosen for polynucleotide-based diagnostic assays. Preferably, two or more of such probes are employed to enhance the hybridization signal corresponding to formation of a duplex between labeled oligonucleotide probes and their complementary target nucleic acids. Use of multiple probes also minimizes false-negative results arising from decreased detection of spurious mutations in a single probe target region.

Preferred methods for detecting the presence of the mecA gene include the step of contacting a test sample under high stringency hybridization conditions with at least two, and preferably at least three, oligonucleotide probes that preferentially hybridize to the mecA gene, and optionally at least one oligonucleotide probe that preferentially hybridizes to a nucleic acid sequence, such as a DNA sequence characteristic of Staphylococcal organisms, over a nucleic acid sequence of other organisms.

While oligonucleotide probes of different lengths and base composition may be used for detecting the mecA gene, preferred probes have lengths of up to 70 nucleotides, and more preferably have lengths of up to 60 nucleotides, and are sufficiently homologous to the target nucleic acid to permit hybridization under high stringency conditions. However, the specific probe sequences described below also may be provided in a nucleic acid cloning vector or transcript or other longer nucleic acid and still can be used for detecting the mecA gene. Thus, the probes may include sequences unrelated to the mecA gene, for instance at the 5' end, at the 3' end, or at both the 5' and 3' ends (as would be the case for molecular beacons and molecular torches). Preferred probes for detecting the mecA gene have sequences of up to 60 nucleotides in length and preferably have at least 17 contiguous nucleotides and more preferably 30 to 35 contiguous nucleotides corresponding to sequences in the mecA gene (see GENBANK Accession No. X52593) or the complement thereof. Preferred oligonucleotide sequences include RNA and DNA equivalents, and may include at least one nucleotide analog.

The probes described herein were tested in hybridization reactions using synthetic targets as well as biological samples, such as *Staphylococcus* isolates, to detect the mecA gene and optionally to identify the genus and/or species of a microorganism present in the biological sample. In one method of determining whether a biological sample contains mecA gene sequences and nucleic acids that would indicate the presence of organisms in the *Staphylococcus* genus, nucleic acids can be released from bacterial cells by addition of a lysing agent, such as a detergent, or by other known methods for disrupting cells including the use of enzymes, osmotic shock, chemical treatment, and vortexing, for instance, with glass beads, or sonic disruption, for example according to the method disclosed in U.S. Pat. No. 5,374,522. Other appropriate methods suitable for liberating nucleic acids from cells have been described in U.S. Pat. No. 5,837,452 and in U.S. Pat. No. 5,364,763. In one preferred embodiment, cells are contacted with a lysis buffer containing a lysing agent.

Preferably, the mecA-specific probes hybridize to mecA DNA sequences only under conditions of high stringency. Under these conditions only highly complementary nucleic acid hybrids will form (i.e., those having at least 14 out of 17 bases in a contiguous series of bases being complementary). Hybrids will not form in the absence of a sufficient degree of complementarity. Accordingly, the stringency of the assay conditions determines the amount of complementarity needed between two nucleic acid strands forming a hybrid. Stringency is chosen to maximize the difference in stability between the hybrid formed with target nucleic acid and non-target nucleic acid.

In one embodiment, probes used for detecting mecA sequences include at least one of SEQ ID NOs:1-6, which have the following sequences:

```
GGTATGTGGAAGTTAGATTGGGATCATAGCG;       (SEQ ID NO: 1)

CGCTATGATCCCAATCTAACTTCCACATACC;       (SEQ ID NO: 2)

GCGATAATGGTGAAGTAGAAATGACTGAACGTCCG;   (SEQ ID NO: 3)

CGGACGTTCAGTCATTTCTACTTCACCATTATCGC;   (SEQ ID NO: 4)

GCTCCAACATGAAGATGGCTATCGTGTCACAATCG;   (SEQ ID NO: 5)
and

CGATTGTGACACGATAGCCATCTTCATGTTGGAGC,   (SEQ ID NO: 6)
respectively.
```

Of course, portions of any of these sequences which preferentially hybridize to the mecA gene or its complement can be used instead. In one embodiment, preferred probes comprise one or more nucleotide analogs comprising a 2'-methoxy ribosyl analog substituted for one or more nucleotides comprising a deoxyribosyl moiety in one of SEQ ID NOs:1-6.

B2. VanA and VanB Probes

Preferred methods for detecting the presence of VanA or VanB gene sequences, for example in an Enterococcal organism, include the step of contacting a test sample under high stringency hybridization conditions with at least one, preferably at least two, and still more preferably at least three, oligonucleotide probes that preferentially hybridize, in aggregate, to the VanA and VanB genes, and optionally at least one oligonucleotide probe that preferentially hybridizes to a nucleic acid sequence, such as a DNA sequence, of Enterococcal organisms over a nucleic acid sequence of other organisms.

While oligonucleotide probes of different lengths and base composition may be used for detecting the VanA and VanB genes, preferred probes have lengths of up to 70 nucleotides, and more preferably have lengths of up to 60 nucleotides, and are sufficiently homologous to the target nucleic acid to permit hybridization under high stringency conditions. However, the specific probe sequences described below also may be provided in a nucleic acid cloning vector or transcript or other longer nucleic acid and still can be used for detecting the VanA and VanB genes. Thus, the probes may include sequences unrelated to the VanA and VanB genes, for instance at the 5' end, at the 3' end, or at both the 5' and 3' ends (as would be the case for molecular beacons and molecular torches). Preferred probes for detecting the VanA and VanB genes have sequences of up to 60 nucleotides in length and preferably have at least 17 contiguous nucleotides and more preferably 30 to 35 contiguous nucleotides corresponding to sequences in the VanA and/or VanB genes, or the complements thereof. Preferred oligonucleotide sequences include RNA and DNA equivalents, and may include at least one nucleotide analog.

In one method of determining whether a biological sample contains VanA and/or VanB gene sequences and nucleic acid that would indicate the presence of members of the *Enterococcus* group, nucleic acids can be released from bacterial cells by addition of a lysing agent, such as a detergent, or by other known methods for disrupting cells including the use of enzymes, osmotic shock, chemical treatment, and vortexing, for instance, with glass beads, or sonic disruption, for example according to the method disclosed in U.S. Pat. No. 5,374,522. Other methods suitable for liberating nucleic acids from cells which can then be subjected to hybridization methods have been described in U.S. Pat. No. 5,837,452 and in U.S. Pat. No. 5,364,763. In one preferred embodiment, cells are contacted with a lysis buffer containing a lysing agent.

Preferably, the probes specifically hybridize to VanA and/or VanB in genomic DNA only under conditions of high stringency. Under these conditions only highly complementary nucleic acid hybrids will form (i.e., those having at least 14 out of 17 bases in a contiguous series of bases being complementary). Hybrids will not form in the absence of a sufficient degree of complementarity. Accordingly, the stringency of the assay conditions determines the amount of complementarity needed between two nucleic acid strands forming a hybrid. Stringency is chosen to maximize the difference in stability between the hybrid formed with target nucleic acid and non-target nucleic acid.

In one embodiment, the probes for detecting the VanA and/or VanB genes include the sequences presented under Example 10, or portions thereof which preferentially hybridize to one of the strands of the VanA and/or VanB genes, or their complements. In various preferred embodiments, probes comprise one or more nucleotide analogs, such as 2'-methoxy ribosyl analogs or base analogs.

C. rDNA Probes rRNA sequences from a collection of related and unrelated organisms can be aligned to identify candidate sequences conserved within a genus that could be used to distinguish Staphylococcal and/or Enterococcal organisms from other bacterial and eukaryotic organisms. Thus, by examination of partial or complete sequences of rRNA or rDNA of various organisms including the Staphylococcal or Enterococcal organisms and unrelated phylogenetic neighbors, aligning the sequences to reveal areas of maximum homology and areas with sequence variation, rRNA or rDNA sequences are identified that are conserved among members of a genus but that exhibit mismatches with rRNA or rDNA sequences of other closely and distantly related genera. Such sequences are then tested against a panel of rRNA or rDNA standards and bacterial lysates to verify their utility as probes under laboratory conditions.

Polynucleotide sequences of rRNAs or rDNAs are most conveniently determined using a dideoxynucleotide sequencing procedure. For rRNA, oligonucleotide primers of about 10-100 bases in length and complementary to conserved regions of rRNA from any of the 5S, 16S or 23S ribosome subunits can be extended by reverse transcriptase. The resulting DNA extension products can then be sequenced by chemical degradation or dideoxynucleotide sequencing (Lane et al., *Proc. Natl. Acad. Sci. USA*, 82:6955 (1985)). According to another method, genomic sequences encoding the rRNA can also be determined.

The strong interdependence of secondary structure and function of the rRNA molecules is well known. Indeed, evolutionary changes in the primary sequence of the rRNA are effectively restricted such that secondary structure of the molecule will be maintained. For example, if a base is changed on one side of a helix of a rRNA molecule, then a compensating change will be made on the other side of the helix to preserve complementarity (this is referred to as covariance). This relationship allows two very different rRNA sequences to be "aligned" based on conserved primary sequence and conserved elements of the secondary structure. Once the sequences have been aligned, it becomes possible to identify conserved and variable regions of the rRNA or rDNA sequence.

Variable regions of rRNAs were identified by comparative analysis using published rRNA sequences and sequences that were determined during the development of the present invention. Commercially available software can be used or adapted for the purposes disclosed herein. Since the sequence evolution at each of the variable regions (for example, spanning a minimum of 10 nucleotides) of rRNA is, for the most part, divergent and not convergent, probes can be based on a few rRNA sequences which differ between the target organism and its phylogenetically closest relatives.

Preferred probes for detecting the rRNA or rDNA of bacteria in the genus *Staphylococcus* have sequences of up to 100 nucleotides in length and have at least 17 contiguous nucleotides, more preferably 30 contiguous nucleotides, and still more preferably 39 contiguous nucleotides contained in the sequence given by GCGATTCCAGCTTCATGTAGTCGAGTTGCAGACTACAATCCGAACTGAGAACAACTTTATGGGATTTGCTTGACCTCGCGGTTTCG (SEQ ID NO:13), e.g., CCGAACTGAGAACAACTTTATGGGATTTGC (SEQ ID NO:10), while CCACTCAAGAGAGACAACATTTTCGACTAC (SEQ ID NO:7) is specific for *S. aureus*rRNA or rDNA. Notably, these probes do not hybridize to ribosomal nucleic acids of bacteria in the genus *Enterococcus* under high stringency hybridization conditions. Preferred oligonucleotide sequences include RNA and DNA equivalents, and may include at least one nucleotide analog.

Preferred hybridization probes for detecting the rRNA or rDNA of bacteria in the group *Enterococcus* have the sequences of CTCCTAGGTGCCAGTCAAATTTTG (SEQ ID NO:14) or CATCATTCTCAATTCCGAGGC (SEQ ID NO:15). Notably, these probes do not hybridize to ribosomal nucleic acids of bacteria in the genus Staphylococcus under high stringency hybridization conditions. In certain embodiments of the invention, the hybridization probes are labeled with a detectable label which allows detection independent of the helper oligonucleotides. Preferred oligonucleotide sequences include RNA and DNA equivalents, and may include at least one nucleotide analog.

Preferred pan-bacterial hybridization probes for detecting the rRNA or rDNA of a plurality of bacterial species have the sequences of CGACAAGGAATTTCGC (SEQ ID NO:16) (which may be synthesized using T-methoxy nucleotide analogs, and which may be used in conjunction with helper oligonucleotides having the sequences of TACCTTAGGACCGTTAT (SEQ ID NO:17) and CAGGTCGGAACTTACC (SEQ ID NO:18)), or GGAACTTACCCGACAAGGAATTTCGCTACCTTAGG (SEQ ID NO:19) (which may be used in conjunction with helper oligonucleotides having the sequences of ACCGTTATAGTTACGGCCGCCGTTTACCGGGGCTTC (SEQ ID NO:20), GCCTGGCCATCATTACGCCATTCGTGCAGGTC (SEQ ID NO:21) and GCCCAAATCGTTACGCCTTTCGTGCGGGTC (SEQ ID NO:22)). Probes having the sequences of SEQ ID No:16 and SEQ ID NO:19 are useful for detecting the ribosomal nucleic acids of a plurality of species of Gram-positive bacteria (including the high(G+C)subset of Gram-positive bacteria), a plurality of species of bacteria in the family Enterobacteriaceae, a plurality of species of bacteria in the genus *Enterococcus*, and a plurality of species of bacteria in the genus *Staphylococcus*. These probes do not hybridize to the nucleic acids of fungal organisms. In certain embodiments of the invention, the hybridization probes are labeled with a detectable label which allows detection independent of the helper oligonucleotides. Preferred oligonucleotide sequences include RNA and DNA equivalents, and may include at least one nucleotide analog.

IV. Helper Oligonucleotides

Hybridization between one or more labeled oligonucleotide probes and a target polynucleotide can be enhanced through the use of unlabeled "helper oligonucleotides" according to the procedure disclosed in U.S. Pat. No. 5,030,557. Helper oligonucleotides bind a region of the target nucleic acid other than the region that is bound by the assay probe. This binding imposes new secondary and tertiary structures on the targeted region of the single-stranded nucleic acid and accelerates the rate of probe binding, and, in some cases, the extent of probe binding.

For example, rRNA possesses tertiary structure arising from the same kind of attractive forces that order duplex DNA into its now well known helical structure. A substantial portion of this secondary and tertiary structure is not lost under conditions normally employed for nucleic acid hybridization, including elevated temperature conditions, the presence of salt, the presence of accelerators, and the like. This residual structure can sterically inhibit, or even block hybrid formation between a nucleotide multimer, for example a DNA or RNA oligomer being used as a probe, and its complementary sequence in the ribosomal RNA or other single stranded nucleic acid such as mRNA or DNA which the probe targets. This inhibition can be reduced or eliminated by use of a "helper" oligonucleotide which binds to a portion of the RNA or DNA other than the portion being targeted by the probe. Interaction with the helper oligonucleotide imposes a new secondary and tertiary structure on the targeted region of the single stranded nucleic acid, and consequently accelerates the rate of probe binding. Thus, by using a properly selected helper oligonucleotide, the rate of hybridization between the probe and its complementary sequence in the targeted nucleic acid can be substantially increased and even permit hybridization to occur at a rate and under conditions otherwise adequate for an assay where, without the use of the helper, no substantial hybridization can occur.

The use of a helper can raise the $T_m$ of the hybrid of a relatively short probe and its intended target relative to the $T_m$ of the hybrid of the probe and a nucleic acid sequence with which the probe is less complementary. As a result, highly specific assays for organisms which occur in environments populated by closely related organisms can be obtained.

Helper oligonucleotides which can be used in combination with detectably labeled oligonucleotide probes are preferably 17 to 100 nucleotides in length. Helper oligonucleotides for use in combination with the above-described *Staphylococcus* genus ribosomal nucleic acid probe include, but are not limited to: UUGACCUCGCGGUUUCG (SEQ ID NO:11) and GCGATTCCAGCTTCATGTAGTCGAGTTG-CAGACTACAAT (SEQ ID NO:12) (see WO 00/667189). Helper oligonucleotides for use in combination with a ribosomal nucleic acid probe specific for *S. aureus*, include but are not limited to: GATGATTCGTCTAATGTCGAC-CTTTGTAACTCC (SEQ ID NO:8) and CGGAATTTCACGTGCTCCGTCGTACTCAGGAT (SEQ ID NO:9). Helper ologonucleotides that can be used in combination with the above-described probe of sequence CTC-CTAGGTGCCAGTCAAATTTTG (SEQ ID NO:14) for detecting the ribosomal nucleic acid of members of the *Enterococcus* genus include, but are not limited to: TCTACGGGGCTTTTACCCTTTCTAGCAGACC (SEQ ID NO:23) and CCTCGTGTTCCGCCGTACTCAGGATC (SEQ ID NO:24). Helper oligonucleotides that can be used in combination with the above-described probe of sequence CATCATTCTCAATTCCGAGGC (SEQ ID NO:15) for detecting the ribosomal nucleic acid of members of the *Enterococcus* genus include, but are not limited to: TAGC-CCTAAAGCTATTTCGGAGAGAACCAGCTATCTCC (SEQ ID NO:25) and CCCTAGTCCAAACAGTGCTCTAC-CTC (SEQ ID NO:26). Helper oligonucleotides that can be used in combination with the pan-bacterial probe having the sequence of CGACAAGGAATTTCGC (SEQ ID NO:16) include, but are not limited to: TACCTTAGGACCGTTAT (SEQ ID NO:17) and CAGGTCGGAACTTACC (SEQ ID NO:18). Helper oligonucleotides that can be used in combination with the pan-bacterial probe having the sequence of GGAACTTACCCGACAAGGAATTTCGCTACCTTAGG (SEQ ID NO:19) include, but are not limited to: ACCGTTAT-AGTTACGGCCGCCGTTTACCGGGGCTTC (SEQ ID NO:20), GCCTGGCCATCATTACGCCATTCGTG-CAGGTC (SEQ ID NO:21) and GCCCAAATCGTTACGC-CTTTCGTGCGGGTC (SEQ ID NO:22). In certain embodiments of the invention, the hybridization probes are labeled with a detectable label which allows detection independent of the helper oligonucleotides. Preferred oligonucleotide sequences include RNA and DNA equivalents, and may include at least one nucleotide analog.

V. Probe Matrix

Results from a probe matrix hybridization procedure can be inputted into a computer or data processor ("computer"), either manually using a keyboard or directly through an interface from an automated device such as a plate reader, film scanner or luminometer. The computer can sort the positive and negative hybridization results for a particular sample to establish a profile that can be compared with a look-up table stored in a memory device linked to the computer. This facilitates associating the hybridization profile with hybridization results obtained using control organisms in order to determine the identity or candidate identity in the case of ambiguous results that are characteristic of more than one organism, and/or the presence or absence of a gene of interest, in the test organism.

It is generally true that the presence of a microorganism in a biological sample will be indicated if the biological sample also contains rRNA or rDNA that is characteristic of the microorganism. Thus, the presence of a particular rRNA or rDNA in a biological sample is diagnostic of the presence of a microorganism that produces that rRNA or rDNA. If a hybridization reaction gives a positive result with a probe specific for Gram-positive bacteria, that result would indicate the presence of one or more species of Gram-positive bacteria in the biological sample. In contrast, a negative result would indicate the absence of Gram-positive bacteria.

*Staphylococcus* genus probe can be used to identify organisms as members of the broad genus of Staphylococcal bacteria, and a species-specific probe can be used independently to identify *Staphylococcus aureus*. Likewise, one or more mecA-specific probes can be used to identify the mecA status of a sample.

*Enterococcus* spp. probes, such as those described herein, can be used for detecting bacterial species that include *E. faecalis* and *E. faecium*. One or more probes able to hybridize the VanA and/or VanB genes can be used to identify the vancomycin-resistance status of a sample.

Of course, a series of positive and negative control hybridizations can be carried out in parallel to ensure validity of the testing results.

VI. Apparatus Useful for Conducting Hybridization Reactions

Examples of formats that can be used to conduct hybridization reactions include, but are by no means limited to: individual tubes each with a different probe or comprising a plurality of probes; the wells of a 96-well or other multi-well microtiter plate; and a solid support such as a dipstick or a "DNA chip" where polynucleotide probes are immobilized to the support at different addresses in a spaced-apart configuration. In one preferred embodiment, the probes are soluble probes. In another preferred embodiment, the probes are immobilized to a solid support. Generally speaking, it is preferred for the various probes used in an apparatus for identifying antibiotic-resistant microorganisms to function under a common set of temperature conditions so that all of the probes can be disposed on a single device. In certain highly preferred embodiments, the probes are used under a single set of hybridization conditions, including a single temperature and/or a single set of ionic strength conditions.

Identifying microorganisms and/or the presence of gene(s) of interest advantageously can be performed without requiring any in vitro amplification step. Alternatively, a preliminary amplification step, for example using transcription mediated amplification (TMA), may be employed (see, e.g., U.S. Pat. No. 5,399,491).

Regardless of whether the probes are soluble or immobilized, in certain preferred embodiments the different probe addresses are maintained spatially separated from each other. For example, probes for detecting Van A target nucleic acids can be disposed in a tube, microtiter well, or immobilized spot in an array that is physically distinct from the tube, microtiter well, or immobilized spot having probes for detecting Van B target nucleic acids. Likewise, for example, probes for detecting the ribosomal nucleic acids of *Staphylococcus aureus* can be physically separated from the probes used for detecting the ribosomal nucleic acids of bacteria in the genus *Enterococcus*. When all of the probe addresses are maintained physically separated from each other, and when the probes are soluble probes rather than probes immobilized in a mircoarray format, the number of hybridization reactions will be increased. Whereas four hybridization reactions were used to conduct the procedure illustrated in Example 13 (which included ambiguous probe addresses for detecting either (a) ribosomal nucleic acids of *S. aureus* or bacteria in the genus *Entercoccus* and (b) Van A or Van B nucleic acids), the number of hybridization reactions would be increased to six if the different probe addresses were separated from each other. In this instance the probes of the six probe addresses would hybridize to nucleic acids from: (1) bacteria in the *Staphylococcus* genus; (2) *S. aureus* bacteria; (3) bacteria in the genus *Enterococcus;* (4) the mecA gene; (5) the Van A gene; and (6)

the Van B gene. Of course, each of these six probe addresses could correspond to a spot in a microarray if the probes are immobilized, and then a single hybridization reaction could be conducted. For example, the different spots in the array could be contained in a single well of a 96-well microtiter plate.

According to one approach for conducting hybridization procedures, probes can be labeled with distinguishable labels. Examples of particularly preferred chemiluminescent labels that can be used for performing the methods described herein are the acridinium ester (AE) labels disclosed in U.S. Pat. No. 5,756,011, the disclosure of which is hereby incorporated by reference. More particularly, a single tube, well, support or address may include distinct probes that are independently labeled with chemiluminescent labels that emit peak energy at different times after generating a light emission. Materials and methods that can be used for making and using distinguishable probes useful in connection with the present invention can be found in U.S. Pat. No. 5,756,011, the disclosure of which is hereby incorporated by reference. Fluorescent labels that produce light at different wavelengths following excitation represent still other examples of distinguishable labels that can be used in connection with the procedures described herein. In this way, two probes that employ distinguishable labels can be distinguished from each other even though they are combined at the same locus of a testing device. Accordingly, it is possible to combine large numbers of different probes at a single address while still being able to distinguish the results of hybridization for the different probes or sets of probes.

In accordance with still another approach, probes with different specificities were labeled with the same label, or with labels that were not distinguished from each other during a step for detecting specific hybrids that include the labeled probe and target, thereby creating an ambiguous result when the probes were combined and when either probe gave a positive hybridization signal.

VII. Kits for Conducting Hybridization Procedures

The materials used for carrying out hybridization procedures in accordance with the invention may be incorporated into kits that can be used for conducting diagnostic procedures. The kits will include at least one device or container containing a plurality of probes for hybridizing nucleic acids from test organisms, and instructions for conducting a nucleic acid hybridization procedure using the probes. The kits optionally may include instructions for detecting specific hybrids between probes that comprise the various addresses, e.g., *Staphylococcus* and/or *Enterococcus* genes, and target genes of interest, e.g., mecA, VanA and/or VanB, obtained from biological samples that undergo testing. In certain embodiments, there also will be included one or more hybridization probes for detecting a broad range of bacterial species.

VIII. Exemplary Detection Assays

In certain preferred embodiments, Hybridization Protection Assays (HPA) may be used to detect an analyte in a medium, where the analyte is part of a specific binding pair. When the medium suspected of containing the analyte is combined with a binding partner, a detectable label attached to the binding partner is capable of undergoing a change in stability or differential degradation whenever the analyte binds to the specific binding partner. In a specific embodiment, single-stranded polynucleotide probes are modified to contain labels at virtually any desired position or location on the probe. In one embodiment, probe labels may be of different stability or susceptible to differential degradation depending on whether the target polynucleotide sequence is hybridized to the probe. In one embodiment, the label on the bound probe is stabilized relative to the label on the unbound probe.

First, binding partners comprising a binding substance and one or more binding partners are selected. These pairs may be polynucleotides or oligonucleotides. In one embodiment, the binding partners are a polynucleotide and one or more oligonucleotides.

Second, the assay format is selected. These may be selected from formats comprising direct binding assays, competition assays, sequential saturation methods, and sandwich assays.

Third, a label is selected for the assay to be performed. This may be a label which can be directly or indirectly detected by colorimetric, fluorimetric, chemiluminescent, or bioluminescent means. The label may have the property that it can be chemically or biochemically degraded so as to modify its ability to be detected, said degradation being possible under conditions which do not adversely effect the binding between the labeled binding partner and its binding substance and other binding partners and binding substances which may participate in the reaction. Preferred labels are ones which are affected in their ability to be detected after exposure to acids, bases, or selective oxidizing agents such as peroxidate, or enzymes.

Fourth, using chemical methods known in the art, the label is attached to the binding substance at a site such that the sensitivity of the label to chemical or biochemical degradation is modified upon interaction of the labeled binding partner with its specific binding substance(s). In some cases several different sites may be tested for label attachment and the site which gives the best differential degradation may be used.

Fifth, the degradation conditions, be they chemical or biochemical, are optimized if needed to give the best detection discrimination of the labeled binding partner in the presence and absence of its binding substance.

Methods for preparing acridinium ester labeled DNA probes and conditions for differential hydrolysis are described in Arnold et al. (*Clin. Chem.* 35:1588 (1989)) and U.S. Pat. No. 6,004,745.

Finally, using the preselected assay format, the ability of the assay system to detect quantitatively or qualitatively the analyte generally employing the steps of: incubating, selectively degrading, and detecting or simultaneously incubating and selectively degrading, and detecting.

Oligonucleotide probes labeled with chemiluminescent acridinium esters are particularly useful for the detection of sequence specific polynucleotides through hybridization. Acridinium esters may be attached at a number of different sites on DNA probes and/or mixed nucleotide/non-nucleotide polymers as described in U.S. application Ser. No. 07/099, 050 filed Sep. 21, 1987. This includes the ability to label the nucleotide bases, the phosphate backbone, the 3' terminus, and the 5' terminus of oligonucleotides as well as the non-nucleotide monomeric units of mixed nucleotide/non-nucleotide polymers. Such acridinium ester labeled probes can show significant differential chemical stability when the probes to which they are attached are free in solution as compared to when they are hybridized.

In one embodiment, at least two probes in a single hybridization reaction are labeled with detectable moieties which are not substantially distinguished from each other during a step for detecting specific hybrids following a hybridization reaction. For example, probes having different specificities may even be labeled with identical detectable labels when the probes are soluble probes that are mixed for use in a single hybridization reaction.

In another embodiment, at least two probes in a single hybridization reaction are labeled with detectable moieties which are distinguishable, e.g., each label comprises components capable of taking part in a distinguishable chemiluminescent reaction (see for instance, U.S. Pat. Nos. 5,656,207 and 5,827,656). Different members of a number of classes of chemiluminescent molecules are capable of exhibiting differences in kinetic and/or spectroscopic properties and can hence be used in the invention, including acridinium and related compounds (e.g., phenanthridinium compounds), phthalhydrazides and related compounds (e.g., naphthalhydrazides), oxalate esters and related compounds and also stabilized dioxetanes and dioxetanones. The variations of compounds within such groups are well-known to those of ordinary skill in the art, likewise it is known that the quantum yield, kinetics and emission wavelengths of their chemiluminescent reactions are affected by their structure. Thus, compounds with high quantum yields, and which, relative to each other possess substantial differences in their reaction rates or their emission wavelengths, in order to maximize the resolution between the detection of these compounds, can be employed. For instance, aryl acridinium esters may be used as labels with appropriate chemical modifications made to produce the desired kinetic and spectroscopic parameters (see, e.g., U.S. Pat. No. 5,656,207).

Thus, probes specific for different genes can be labeled with different labels, the labeled probes can be mixed and allowed to hybridize to any nucleic acid contained in the test sample having a sequence sufficiently complementary to the probe sequence to allow hybridization under appropriately selective conditions. In one embodiment, one or more reagents are added to the solution which will specifically alter the labeling reagent associated with unhybridized labeled probe while leaving the labeling reagent associated with the hybridized probes substantially unaltered. This allows each labeling compound to be differentially resistant to loss of chemiluminescent potential depending on whether the label is associated with a hybridized or unhybridized probe. In a preferred embodiment, the hybridized probe associated label is so protected (see, for instance, U.S. Pat. No. 5,827,656).

Such labeling reagents are particularly useful in, although not limited to, homogeneous assay systems in which analytes of interest may be detected and measured without the need for the analyte-bound label to be physically separated from the unbound label prior to detection. However, such reagents may be used in heterogeneous systems or in combinations of homogeneous and heterogenous assay systems as well.

Notably, oligonucleotides, or the complements thereof, which are disclosed herein as probes also may be used as primers in amplification reactions. For example, primers having the target-complementary sequences of SEQ ID NO:4 and SEQ ID NO:6 were used in PCR reactions to amplify mecA sequences. Example 11 illustrates the use of probe sequences as primer sequences to amplify nucleic acids diagnostic of resistance to vancomycin.

The invention will be further described by the following non-limiting Examples.

Example 1

Initial Evaluation of Probes for Detecting the mecA Gene

Two probes were designed to hybridize at nucleotides 501 to 531 of the mecA gene sequence: probe 2, CGCTATGATC-CCAATCTAACTTCCACATACC (SEQ ID NO:2) was designed to hybridize one strand of the mecA gene, and probe 1, GGTATGTGGAAGTTAGATTGGGATCATAGCG (SEQ ID NO:1), was designed to hybridize to the opposite strand of the mecA gene. The probes were synthesized by standard phosphoramidite procedures with an internal non-nucleotide linker inserted between nucleotide positions 21 and 22, and between positions 13 and 14, respectively using the procedure disclosed in U.S. Pat. No. 5,656,744. The probes were labeled with an acridinium ester (AE) according to the method disclosed in U.S. Pat. No. 5,185,439 and used for testing biological samples.

Two S. aureus isolates were obtained from an outside laboratory which reported one specimen (#99) to be mecA-positive by a diagnostic PCR assay (Murakami and Minamide, In: Diagnostic Molecular Microbiology, D. Pershing et al., Eds., American Society for Microbiology, 1993, pp. 539-541) and the other (#100) mecA-negative by PCR. Both specimens were reported to have an Oxacillin Minimum Inhibitory Concentration ("Ox MIC") of 4 µg/ml, a value considered unusually high for a mecA-negative specimen.

The specimens were lysed by suspending approximately $5 \times 10^8$ cells in a lysis buffer (0.1% lithium lauryl sulfate, 1 mM EDTA, 20 mM lithium succinate, pH 5.5) and then incubating in a heat block set at 110° C. for 20 minutes. Thermal lysis of a variety of other specimens was effected under a range of temperature (heat block set at about 95° C. to 110° C.) and time (about 10 to 25 minutes) conditions. The lysed samples were tested for the presence of target sequences complementary to the probes using a Hybridization Protection. Assay (HPA) as described by Arnold et al., in Clin. Chem. 35:1588(1989) and U.S. Pat. No. 6,004,745. 50 µl of the heat-treated suspension was incubated with an equal volume of AE-labeled probe in 2× hybridization buffer (1.2 M LiCl, 2% lithium lauryl sulfate, 20 mM EDTA, 20 mM EGTA, 100 mM lithium succinate, pH 5.5) at 60° C. for 30 minutes. The pH of succinate solutions may range from about 4.5 to about 5.5, although it is desirable to use a pH of 4.8 for succinate buffering. 300 µl of a selection reagent (0.6 M borate buffered solution, pH 8.5; note, pH may vary from 8.0 to 9.0) was added, the mixture was heated at 60° C. for 10 minutes to effect differential hydrolysis, and the samples were read in a GEN-PROBE® LEADER° luminometer using sequential 300 µl injections of 0.1% $H_2O_2$ and 1 N NaOH solutions (see Arnold et al, supra; GEN-PROBE® Detection Reagent Kit, Cat. No. 1791 may be used).

Representative test results for the two probes with specimens #99 and #100 are provided in Table 1.

TABLE 1

Probe Hybridization Confirms the Results of Diagnostic PCR Assays

| Test Sample | mecA PCR | Ox MIC (µg/ml) | AE-probe Average RLU Probe 1 | Probe 2 |
| --- | --- | --- | --- | --- |
| No Specimen | — | — | 431 | 3062 |
| #100 | Neg | 4 | 590 | 5585 |
| #99 | Pos | 4 | 2664 | 8072 |

The results presented in Table 1 showed that specimen #100 was mecA(−) and that specimen #99 was mecA(+), thereby confirming the results obtained using a diagnostic PCR assay. However, the cell load used in this Example was near the limit of detection for direct probe detection. This was more noticeable in the trial that included probe 2, as evidenced by a high background signal that made interpretation somewhat difficult at this level of cell load. Conversely, probe 1 was found to give more definitive results, perhaps as the result of a substantially lower background signal.

Example 2

Use of a Pan-Bacterial Probe as a Positive Control

Procedures similar to those described in Example 1 were conducted using a large number of bacterial samples, except that parallel hybridization reactions employed a pan-bacterial probe which targeted rRNA (Probe Reagent 1, GEN-PROBE® MTC-NI Kit, catalog no. 4573). The PCR-negative specimens had abnormally high Ox MIC levels, and one PCR-positive specimen had a very low Ox MIC value. The pan-bacterial probe reagent served as a positive control for lysis of all of the specimens. In this procedure each sample was tested against a panel of the three probes contained in separate hybridization reactions. Aliquots of the samples tested using the pan-bacterial probe reagent were diluted 1:3000 prior to performing luminometry so that results fell within the linear range of the detector. The signals indicated lysis and detection of ribosomal nucleic acids in each of the samples. These values depended on the number of bacterial cells in the specimen, as well as on the extent of cell lysis and the release or accessibility of ribosomal nucleic acids from the cells to be detected by the pan-bacterial probe.

The results for various specimens are shown in Table 2.

TABLE 2

Hybridization Results Obtained Using mecA and Pan-Bacterial Probes

| Test Sample | mecA PCR | Ox MIC µg/ml | AE-Probe Signal (RLU) | | |
|---|---|---|---|---|---|
| | | | Probe 1 | Probe 2 | Pan-Bacterial* |
| Negative Control | NA | NA | 1817 | 1931 | 350 |
| rRNA Pos. Control | NA | NA | NA | NA | 52141 |
| 10 | Neg | 8 | 2918 | 3274 | 50408* |
| 100 | Neg | 4 | 815 | 6186 | 24006* |
| 101 | Neg | 4 | 2768 | 6266 | 45639* |
| 103 | Neg | 4 | 1097 | 2366 | 27138* |
| 104 | Neg | 2 | 959 | 2000 | 31212* |
| 105 | Neg | 2 | 1086 | 2714 | 13699* |
| 106 | Neg | 2 | 1327 | 2989 | 32059* |
| 145 | Neg | 4 | 997 | 2788 | 19564* |
| 155 | Neg | 4 | 730 | 2257 | 41384* |
| 164 | Neg | 2 | 1546 | 3287 | 41698* |
| 99 | Pos | 4 | 5822 | 13021 | 35354* |
| 102 | Pos | 4 | 5623 | 13065 | 36721* |
| 139 | Pos | 4 | 5755 | 9563 | 29994* |
| 140 | Pos | 16 | 3143 | 4967 | 17506* |
| 142 | Pos | 4 | 6845 | 10345 | 29905* |
| 148 | Pos | 4 | 10483 | 15878 | 66145* |
| 178 | Pos | 2 | 7772 | 12652 | 41643* |
| 188 | Pos | 2 | 11856 | 20757 | 41605* |
| 270 | Pos | <0.25 | 9256 | 14965 | 23183* |
| 296 | Pos | Lab Pos control | 5567 | 10585 | 23240* |

*(diluted 1:3000 prior to luminometry)

The results presented in Table 2 showed that both of the mecA-specific probes gave positive, but relatively weak, signals for specimens that were positive for the mecA gene by the diagnostic PCR assay. Equivocal results that were obtained using probe 2 with one PCR-positive and two PCR-negative specimens may have been due, in part, to the relatively high background of probe 2 and to the sensitivity limitation imposed by using a single probe to test the specimens at the levels of cells in the sample. Additionally, the mecA probes required denaturation and accessibility to ssDNA containing the gene target region to obtain the optimal detection signal. In contrast, rRNA detected by the pan-bacterial probe reagent is available in substantial quantities per cell compared to DNA, and the accessibility of the rRNA target region for hybridization and detection by the probe reagent was assisted by the inclusion of helper probes (Hogan et al., U.S. Pat. No. 5,030,557) in that reagent. Detection of rRNA would not be indicative of the amount or reactivity of a ssDNA target region with regard to accessibility or kinetics of hybridization. Instead, it would indicate success of the lysis procedure.

Example 3

Base Treatment of Specimens

Treatment of specimens under alkaline conditions was investigated as a means for denaturing nucleic acids and making target sequences available for hybridization with the detection probe(s). Base treatment offered the further possible advantage of hydrolyzing RNA so that positive internal control hybridization probes more properly detect ribosomal DNA (rDNA) targets, thereby permitting more direct comparison between results obtained using the mecA probe and the control probe. Base treatment to lyse cells and degrade RNA depends on hydroxide concentration, temperature and incubation time. Notably, probes designed to detect rRNA are also capable of detecting the corresponding rDNA target.

The effect of base treatment on a *S. aureus* specimen (#102) was evaluated using the pan-bacterial probe reagent. A pelleted sample of the specimen was suspended in 120 µl of lysis buffer and lysed by treatment for 20 minutes in a heat block set at 110° C. A 50 µl aliquot of the lysed specimen was treated with 50 µl of a 0.4 N LiOH solution at 55° C. for 10 minutes, and then neutralized with the addition of 50 µl of 0.4 N HCl and buffered with 50 µl of a 1× hybridization buffer (0.6 M LiCl, 1% lithium lauryl sulfate, 10 mM EDTA, 10 mM EGTA, 50 mM lithium succinate, pH 5.5). The treated sample was hybridized with the AE-labeled pan-bacterial probe by incubating at 55° C. for 1 hour. An HPA assay to detect specific probe hybrids was carried out using standard procedures that will be familiar to those having an ordinary level of skill in the art. A control sample consisted of 50 µl of the lysed specimen and volumes of hydrolysis, neutralization and buffered solutions equivalent to those of the treated sample.

The results of base treatment of a *S. aureus* specimen using a pan-bacterial probe reagent are shown in Table 3.

TABLE 3

Base Treatment Reduces the Hybridization Signal Obtained Using the Pan-Bacterial Probe

| Sample | Sample Volume Read | Pan-Bacterial Probe Signal (RLU) |
|---|---|---|
| #102, Control (no base treatment) | 50 µl † | 483845 |
| #102, Base Treated | 300 µl | 134426 |

† ⅙ of the volume was used to bring the control signal into the range of the luminometer.

The results presented in Table 3 showed evidence for significant, but perhaps incomplete, degradation of the rRNA target under the condition tested since both rDNA and residual rRNA targets could have contributed to the chemiluminescent signal measured in the hydrolyzed sample. Higher base concentrations, longer incubation times, and higher temperatures showed increased degradation of the signal. For example, the effect of base treatment with 0.8 N LiOH for 10 minutes at 55° C. was assessed using AE-probe 1. For these treatments, an equal volume of 0.8 N LiOH was added to the sample, and the reaction mixtures were neutralized with the addition of an equivalent volume of 0.8 N HCl prior to buffering and assaying by HPA. 300 µl aliquots of each reaction mixture were read in the luminometer. These procedures employed a single-stranded DNA oligonucleotide having the same sequence that was present in the target bacteria, and that was fully complementary to the hybridization probe undergoing testing, as synthetic target.

TABLE 4

Enhanced Base Treatment of the Target Does Not Compromise Hybridization of the mecA Probe

| Sample | AE-probe 1 Signal (RLU) |
|---|---|
| Synthetic target, Control (no base treatment) | 22195 |
| Synthetic target, base treated | 21283 |
| #148, Control (no base treatment) | 34677 |
| #148, base treated | 42627 |
| Synthetic target + #148, Control | 53367 |
| Synthetic target + #148, base treated | 58565 |

The results shown in Table 4 indicated that there was very little, if any, loss of signal due to degradation of target DNA sequences under the base treatment conditions that were tested.

Example 4

Base Treatment and Lysis

The effect of base treatment with and without the heat treatment in lysis buffer was evaluated using a *S. aureus* specimen (GP1217, ATCC #33591). In this procedure the sample was treated with 0.8 N LiOH and thermal lysis was conducted by heat treatment for 15 minutes. Other conditions were as described above. Probe 1 labeled with acridinium ester was used in this procedure.

TABLE 5

Bacterial Sample Preparation

| Sample | Probe 1 RLU | Pan-Bacterial RLU |
|---|---|---|
| Negative Control | 592 | 3891 |
| Positive Control | nd | 51752 |
| GP1217, Thermal lysis 15 minutes at 100° C. + Base treatment 15 minutes at 60° C. | 38017 | 514600 |
| GP1217, Base treatment 30 minutes at 60° C. | 16016 | 66871 |

The results presented in Table 5 indicated that base treatment under the specified conditions was adequate to lyse cells and render the target sequence available for detection by the labeled hybridization probe.

A range of base treatment conditions were found to be effective for this purpose. For example, hydroxide at a final concentration of about 0.2-0.4 N, temperatures of about 55° C. to about 60° C., and incubation times of about 5 to 30 minutes all gave good results in the procedure. Accordingly, a wide range of conditions may be used for base treatment of specimens including, but not limited to, final base concentrations of about 0.2 N to about 1 N in hydroxide, temperatures from about 50° C. to about 60° C., and incubation times of about 5 minutes to about 30 minutes. Of course, conditions involving lower hydroxide concentrations and higher temperature incubations are contemplated as part of the invention. Generally speaking, a temperature range of from about room temperature up to about 100° C. with different base concentrations are contemplated for sample preparation steps that fall within the scope of the invention.

Example 5

Internal Controls

*Staphylococcus aureus* Probe and Helpers

```
Probe
SauB338:
CCACTCAAGAGAGACAACATTTTCGACTAC.     (SEQ ID NO: 7)
```

SauB338-AE(20/21): This probe had the sequence of SEQ ID NO:7, and was labeled with acridinium ester attached to a non-nucleotide linker inserted between nucleotide positions 20 and 21

```
Helpers
SauB278:
GATGATTCGTCTAATGTCGACCTTTGTAACTCC   (SEQ ID NO: 8)

SauB368:
CGGAATTTCACGTGCTCCGTCGTACTCAGGAT    (SEQ ID NO: 9)
```

*Staphylococcus* Genus Probe and Helpers

```
Probe
SauA1276:
CCGAACTGAGAACAACTTTATGGGATTTGC.     (SEQ ID NO: 10)
```

SauA1276-AE(19/20): This probe had the sequence of SEQ ID NO:10, and was labeled with acridinium ester attached to a linker inserted between nucleotide positions 19 and 20.

```
Helpers
MeO-SauA1259:
                                    (SEQ ID NO: 11)
UUGACCUCGCGGUUUCG
(2-methoxy nucleotide analogs were used to
synthesize this helper oligonucleotide)

SauA1306:
                                    (SEQ ID NO: 12)
GCGATTCCAGCTTCATGTAGTCGAGTTGCAGACTACAAT
```

Methicillin-resistant (mecA-positive) *S. aureus* ("MRSA") isolates GP1217 (ATCC #33591) and GP1218 (ATCC #43866), and methicillin-susceptible (mecA-negative) *S. aureus* ("MSSA") isolates GP1214 (ATCC #29247) and GP18 (ATCC #12600), were grown on TSA plates (Hardy Diagnostics, Cat. No. A-10) overnight at 37° C. and used as specimens for testing the *S. aureus* probe and helpers identified by SEQ ID NOs:7-9 (Milliman, U.S. Pat. No. 5,292,874), and the *Staphylococcus* spp. probe and helpers identified by SEQ ID NOs:10-12 (Hogan et al., U.S. Pat. No. 6,376,186) as internal controls for adequate presence of target organisms in the specimen and to determine whether the specimen is *S. aureus* or a coagulase-negative *Staphylococcus* spp. ("CoNS").

The cultured *S. aureus* specimens were lysed by suspending 1 µl loops of bacteria in 150 µl of lysis buffer and then incubating at 105° C. for 15 minutes. Next, 100 µl of 2 N LiOH base solution was added and RNA was hydrolyzed by incubating the mixtures at 60° C. for 15 minutes. Hydrolyzed samples were neutralized by the addition of 100 µl of a neutralizing reagent that included 2 N HCl and 100 mM succinate buffer (pH 5.5 prior to acidification with HCl). Specifically hybridized probe was detected by standard HPA, essentially as described in Example 1.

Test results using *S. aureus* and *Staphylococcus* genus probes with helper probes for four specimens are provided in Table 6.

TABLE 6

Taxonomic Probes Used in Combination with a mecA-Specific Probe Provide Greater Functionality in Probe Panels

| Probe Composition | GP1217 (Pos) RLU | GP1218 (Pos) RLU | GP1214 (Neg) RLU | GP18 (Neg) RLU |
|---|---|---|---|---|
| probe 1 (mecA) | 53,322 | 36,730 | 848 | 821 |
| S. aureus probe with helpers | 199,476 | 163,825 | 203,725 | 148,780 |
| Staphylococcus spp. probe with helpers | 225,772 | 203,488 | 234,286 | 170,434 |

The results presented in Table 6 exactly matched the expected hybridization patterns for all four samples. More specifically, the *Staphylococcus* spp. probe, that was specific for a plurality of members of the *Staphylococcus* genus, gave positive hybridization signals for all samples. This indicated that all samples contained *Staphylococcus* bacteria, as expected. Additionally, all four samples gave positive hybridization signals when hybridized with the probe specific for *S. aureus*. This indicated that all samples contained *S. aureus* bacteria. Finally, only the mecA positive specimens and not the mecA-negative specimens gave positive hybridization signals with mecA-specific probe 1.

These results defined a highly desirable panel of hybridization probes useful for determining the identity and methicillin resistance status of bacteria undergoing testing. In one embodiment, the invention includes a probe that is specific for a plurality of bacteria in the *Staphylococcus* genus, including *S. aureus* and *S. epidermidis*. It is highly preferred that this probe is specific for ribosomal nucleic acids of the target bacteria. Also present in the panel is a probe that specifically hybridizes to the nucleic acids of *S. aureus*, but not to the nucleic acids of other bacteria in the *Staphylococcus* genus, such as *S. epidermidis*. It is highly preferred that this probe is specific for ribosomal nucleic acids of *S. aureus*. Further, it is preferred that the panel include a probe that hybridizes to the mecA gene or the RNA transcript encoded by the mecA gene. This mecA-specific probe should not hybridize to other drug resistance markers, such as the genes encoding resistance to vancomycin.

As indicated in the following Example, alternative probe sequences can be used for detecting the mecA gene in a sample containing nucleic acids.

Example 6

Evaluation of Additional mecA Gene Probes

Probes
Probe 3:
GCGATAATGGTGAAGTAGAAATGACTGAACGTCCG  (SEQ ID NO: 3)

Probe 4:
CGGACGTTCAGTCATTTCTACTTCACCATTATCGC  (SEQ ID NO: 4)

Probe 5:
GCTCCAACATGAAGATGGCTATCGTGTCACAATCG  (SEQ ID NO: 5)

Probe 6:
CGATTGTGACACGATAGCCATCTTCATGTTGGAGC  (SEQ ID NO: 6)

To increase the sensitivity of mecA detection, additional probes were designed that corresponded to nucleotide bases 304-338 and 1010-1044 of the mecA gene. These probes flanked probe 1 and probe 2. Probe 3 (SEQ ID NO:3, complementary to the antisense (−) strand of the mecA gene) was labeled with AE attached by a linker positioned between bases 16 and 17. Probe 4 (SEQ ID NO:4, complementary to the sense (+) strand of the mecA gene) was labeled with AE attached by a linker positioned between bases 15 and 16. Probe 5 (SEQ ID NO:5, complementary to the antisense (−) strand of the mecA gene) was labeled with AE attached by a linker positioned between bases 20 and 21. Probe 6 (SEQ ID NO:6, complementary to the sense (+) strand of the mecA gene) was labeled with AE through a linker attached between bases 23 and 24.

Procedures

Specimens (1 μl loops of bacteria) were treated and tested essentially as described in Example 5 with the following differences: incubation for lysis was for 15 minutes and incubation for hybridization was for 45 minutes for samples shown in Tables 7-8, while incubation for lysis was for 10 minutes and incubation for hybridization was for 20 minutes for samples shown in Table 9. All of the base-treated solutions were neutralized by the addition of 250 μl of 0.8 N HCl containing 100 mM succinate.

The specimen testing results with probe 3-6, alone and in mixtures, are presented in Tables 7-9.

TABLE 7

Testing of Additional mecA-Specific Probes

| Probe Composition | Probe alone Avg RLU | GP1217 (Pos) RLU | GP18 (Neg) RLU |
|---|---|---|---|
| probe 1 | 3668 | 25928 | 757 |
| probe 6 | 6117 | 38158 | 1195 |
| probe 5 | 4088 | 37472 | 1250 |
| probe 1 + probe 6 | 4098 | 63676 | 2193 |
| probe 1 + probe 5 | 2821 | 72033 | 1771 |

TABLE 8

Testing of Additional mecA-Specific Probes

| Probe Composition | Probe alone Avg RLU | GP1217 (Pos) RLU | GP18 (Neg) RLU |
|---|---|---|---|
| probe 1 | 1123 | 11485 | 879 |
| probe 4 | 690 | 20192 | 641 |
| probe 3 | 445 | 36123 | 371 |
| probe 1 + probe 4 | 1493 | 41537 | 928 |
| probe 1 + probe 3 | 1296 | 63175 | 844 |

TABLE 9

Testing of Additional mecA-Specific Probes

| Probe Composition | Probe alone Avg RLU | GP1217 (Pos) RLU |
|---|---|---|
| probe 1 | 2476 | 27256 |
| probe 4 | 734 | 34352 |
| probe 3 | 684 | 46566 |
| probe 6 | 1004 | 55947 |
| probe 5 | 2823 | 42816 |
| probe 4 + probe 6 | 1443 | 93569 |
| probe 3 + probe 5 | 12014 | 97324 |
| probe 1 + probe 4 + probe 6 | 3064 | 115414 |
| probe 1 + probe 3 + probe 5 | 11759 | 121633 |

The results presented in Tables 7-9 showed that probes directed to additional target regions gave good specificity with desirably low backgrounds. Mixtures of the probes showed enhanced signals, although some combinations with high backgrounds may indicate undesirable probe interactions.

Example 7

2'-Deoxy and 2'-Methoxy Probe Mixtures

2'-methoxy analogs of the AE-labeled DNA probes were prepared by standard phosphoramidite synthesis using 2' methoxy phosphoramidite analogs. Additional linker positions, which are indicated by parentheses in Table 11, for probe 2 were also prepared for testing. Deoxy probes and 2'-methoxy probe analogs were tested essentially as described in Example 5, except as noted below. The results are provided in Tables 10-12. Probes synthesized using 2'-methoxy nucleotide analogs are particularly identified by the "MeO" designations. Brief summaries of the procedures used to obtain the results are appended to the tables.

TABLE 10

Probe Combinations and the Use of Nucleotide Analogs Can Further Improve Probe Performance

| Probe Composition | Probe alone Avg RLU | GP1217 (Pos) RLU | GP1214 (Neg) RLU |
| --- | --- | --- | --- |
| probe 1 | 2131 | 37695 | 1844 |
| MeO-probe 2 | 2378 | 69687 | 5242 |
| MeO-probe 1 | 1879 | 62594 | 2308 |
| MeO-probe 1 + probe 3 | 2732 | 94942 | 2504 |
| MeO-probe 1 + probe 6 | 3915 | 89312 | 9797 |
| probe 3 + probe 6 | 3745 | 105024 | 3606 |
| MeO-probe 1 + probe 3 + probe 6 | 4247 | 146128 | 4684 |

1 µl loop S. aureus in 150 µl lysis reagent, incubate for 10 minutes at 105° C.
base treatment: 100 µl 2 N hydroxide, incubate for 10 minutes at 60° C.
neutralize: 100 µl 2 N HCl containing 200 mM succinate
hybridize: 45 minutes at 60° C.

TABLE 11

Numerous Labeling Positions Yield Useful Probes

| Probe Composition | Probe alone Avg RLU | GP1217 (Pos) RLU | GP1214 (Neg) RLU |
| --- | --- | --- | --- |
| (13,14)-MeO-probe 1 | 779 | 33659 | 975 |
| (4,5)-MeO-probe 2 | 665 | 52714 | 1852 |
| (14,15)-MeO-probe 2 | 829 | 48954 | 6327 |
| (17,18)-MeO-probe 2 | 825 | 55066 | 3406 |
| (16,17)-probe 3 | 1098 | 36993 | 1303 |
| (16,17)-MeO-probe 3 | 1287 | 60095 | 997 |
| (15,16)-MeO-probe 4 | 579 | 56497 | 1185 |
| (23,24)-probe 6 | 1540 | 43307 | 1994 |
| (23,24)-MeO-probe 6 | 2370 | 70180 | 5015 |
| (20,21)-MeO-probe 5 | 815 | 60009 | 1809 |

1 µl loop S. aureus in 150 µl lysis reagent, incubate for 10 minutes at 105° C.
base treatment: 100 µl 2 N hydroxide, incubate for 10 minutes at 60° C.
neutralize: 250 µl 0.8 N HCl containing 100 mM succinate
hybridize: 45 minutes at 60° C.

Further testing results for AE (4,5)-MeO-probe 2 are shown in Table 12.

TABLE 12

Variously Positioned Labels Yield Useful Probe Compositions

| Probe Composition | Probe alone Avg RLU | GP1217 (Pos) RLU | GP1214 (Neg) RLU |
| --- | --- | --- | --- |
| (4,5) MeO-probe 2 + MeO-probe 4 | 4840 | 132167 | 6689 |
| (4,5)-MeO-probe 2 + probe 6 | 4349 | 132124 | 6059 |
| MeO-probe 4 + probe 6 | 2723 | 138838 | 5552 |
| (4,5)-MeO-probe 2 + probe 4 + probe 6 | 6841 | 196585 | 10082 |
| MeO-probe 3 + probe 5 | 992 | 133327 | 2461 |
| (4,5)-MeO-probe 2 + probe 3 + probe 5 | 2260 | 208346 | 4563 |
| (4,5)-MeO-probe 2 + probe 3 + probe 6 | 3365 | 202877 | 6203 |
| (4,5)-MeO-probe 2 + probe 4 + probe 5 | 7537 | 209019 | 7742 |

1 µl loop S. aureus in 150 µl lysis reagent, incubate for 10 minutes at 105° C.
base treatment: 100 µl 2 N hydroxide, incubate for 10 minutes at 60° C.
neutralize: 250 µl 0.8 N HCl containing 100 mM succinate
hybridize: 20 minutes at 60° C.

These results showed that methoxy nucleotide analogs gave modestly increased signals with mecA-negative samples, but substantially higher signals when hybridized to nucleic acids prepared from methicillin-resistant organisms. Mixtures of the probes resulted in significantly higher signals. Various combinations of the probes gave good results.

Example 8

Testing Clinical Specimens

The results of testing clinical isolates with a combination of mecA probes are shown in Table 13. Oxacillin MIC and Oxoid PBP2' Latex Agglutination ("OLA") test results were determined at the collection site prior to shipment of the samples for the determination of mecA gene status. 1 µl loops of the specimens at the collection site were suspended in 150 µl of lysis reagent and incubated for 10 minutes at 100° C., and then followed by freezing. For HPA determinations, the samples were thawed, vortexed and incubated at 100° C. for 5 minutes. Each sample received a 100 µl aliquot of 2 N LiOH, and was subsequently incubated at 60° C. for 10 minutes. Samples were neutralized by adding 100 µl of 2 N HCl containing 200 mM succinate buffer. Aliquots of the reaction mixture were then assayed by HPA as described in Example 1. The Gen-Probe ("GP") HPA Staphylococcus spp. and S. aureus RLU values were determined using the probes and helper oligonucleotides described in Example 5, except that the S. aureus results were determined using an AE-labeled S. aureus probe (SEQ ID NO:7) having a linker inserted between positions 22 and 23 instead of between positions 20 and 21. The mecA status was determined using a mixture of AE-labeled probes (i.e., (4,5)-2'-OMe-probe 2, (16,17)-probe 3 and (20,21)-probe 5).

TABLE 13

Testing Clinical Specimens Using a Probe Panel

| Sample | HPA Results (RLU) | | | Oxacillin MIC (µg/ml) | Oxoid (OLA) | Identity |
|---|---|---|---|---|---|---|
| | Staph Spp | S. aureus | mecA | | | |
| Neg Control | 1775 | 3472 | 1390 | nd | nd | Hybridization Buffer |
| Pos Control GP1217 | 170530 | 162795 | 145716 | >16 | Pos | S. aureus, mecA(+) (MRSA) |
| GP21 | 373232 | 351348 | 3429 | <0.25 | Neg | S. aureus, mecA(−) (MSSA) |
| GP22 | 225141 | 7637 | 210788 | 0.5 | Pos | CoNS, mecA(+) |
| GP23 | 301657 | 280428 | 3562 | <0.25 | Neg | S. aureus, mecA(−) |
| GP24 | 306718 | 274112 | 265780 | >16 | Pos | S. aureus, mecA(+) |
| GP25 | 456426 | 408938 | 456055 | >16 | Pos | S. aureus, mecA(+) |
| GP26 | 262267 | 241597 | 3309 | <0.25 | Neg | S. aureus, mecA(−) |
| GP27 | 182304 | 7057 | 3886 | <0.25 | Neg | CoNS, mecA(−) |
| GP28 | 246636 | 195759 | 41183 | 1 | Neg | S. aureus, mecA(−) |
| GP29 | 388748 | 416372 | 440128 | >16 | Pos | S. aureus, mecA(+) |
| GP30 | 440128 | 399498 | 5660 | <0.25 | Neg | S. aureus, mecA(−) |
| GP31 | 349207 | 332750 | 322837 | >16 | Pos | S. aureus, mecA(+) |
| GP32 | 432041 | 414709 | 11706 | <0.25 | Neg | S. aureus, mecA(−) |
| GP33 | 160830 | 154183 | 142431 | >16 | Pos | S. aureus, mecA(+) |
| GP34 | 634079 | 497890 | 5191 | <0.25 | Neg | S. aureus, mecA(−) |
| GP35 | 543089 | 484580 | 370770 | >16 | Pos | S. aureus, mecA(+) |
| GP36 | 370898 | 356243 | 5587 | <0.25 | Neg | S. aureus, mecA(−) |
| GP37 | 397722 | 373448 | 406010 | >16 | Pos | S. aureus, mecA(+) |
| GP38 | 387613 | 367728 | 402740 | nd | Pos | S. aureus, mecA(+) |
| GP39 | 280358 | 268665 | 4838 | <0.25 | Neg | S. aureus, mecA(−) |
| GP40 | 292407 | 283200 | 3617 | <0.25 | Neg | S. aureus, mecA(−) |

The results presented in Table 13 demonstrated that the invented hybridization assay correctly identified the organism type and methicillin-resistance status for numerous clinical isolates. The unusual result obtained for the GP28 sample, meaning an intermediate mecA hybridization signal coupled with an intermediate MIC reading, could not be repeated and was attributed to unreacted probe that was not efficiently hydrolyzed by the selection reagent. The high background HPA result would easily be explained by incomplete mixing of the probe and selection reagent during the HPA procedure.

Example 9

Additional Specimen Testing

Additional testing of isolates is summarized in Table 14. Oxacillin MIC results were provided by an outside laboratory. The GP Probe results were determined as described in Example 8.

TABLE 14

Testing Clinical Specimens Using a Probe Panel

| Organism | # Isolates | Oxacillin MIC (µg/ml) | HPA Results (# positive for indicated probes) | | | | OLA | |
|---|---|---|---|---|---|---|---|---|
| | | | Staph. Spp. | S. aureus | mecA (+) | mecA (−) | Pos | Neg |
| Clinical MRSA | 14 | 4 | 14 | 14 | 6 | 8 | 6 | 8 |
| | 13 | 8 | 13 | 13 | 9 | 4 | 9 | 4 |
| | 8 | 16 | 8 | 8 | 8 | 0 | 7 | 1 |
| | 107 | >16 | 107 | 107 | 107 | 0 | 106 | 1 |
| Clinical MSSA | 99 | ≤0.25 | 99 | 99 | 1 | 98 | 1 | 98 |
| | 28 | 0.5 | 28 | 28 | 0 | 28 | 0 | 28 |
| | 13 | 1 | 13 | 13 | 0 | 13 | 0 | 13 |
| | 8 | 2 | 8 | 8 | 2 | 6 | 2 | 6 |
| ATCC MRSA | 1 | 8 | 1 | 1 | 1 | 0 | 1 | 0 |
| | 1 | 16 | 1 | 1 | 1 | 0 | 1 | 0 |
| ATCC MSSA | 6 | ≤0.25 | 6 | 6 | 0 | 6 | 0 | 6 |
| | 4 | 0.5 | 4 | 4 | 0 | 4 | 0 | 4 |
| | 1 | 1 | 1 | 1 | 0 | 1 | 0 | 1 |
| S. epidermidis | 2 | ≤0.25 | 2 | 0 | 0 | 2 | 0 | 2 |
| | 1 | 4 | 1 | 0 | 1 | 0 | 1 | 0 |
| | 1 | >16 | 1 | 0 | 1 | 0 | 1 | 0 |
| S. intermedius | 1 | ≤0.25 | 1 | 0 | 0 | 1 | 0 | 1 |
| S. hyicus-hyicus | 1 | ≤0.25 | 1 | 0 | 0 | 1 | 0 | 1 |
| S. warneri | 1 | ≤0.25 | 1 | 0 | 0 | 1 | 1 | 0 |
| S. hemoliticus | 1 | ≤0.25 | 1 | 0 | 0 | 1 | 0 | 1 |
| S. saprophyticus | 1 | 0.5 | 1 | 0 | 0 | 1 | 0 | 1 |
| S. simulans | 1 | ≤0.25 | 1 | 0 | 0 | 1 | 0 | 1 |
| S. hominis | 1 | ≤0.25 | 1 | 0 | 0 | 1 | 0 | 1 |

The results in Table 14 showed that the Oxoid (OLA) test missed detecting some of the clinical mecA(+) *S. aureus* samples. The fact that false-negative results were obtained in the OLA assay was supported by the results of the MIC assay. Additionally, the OLA assay gave false-positive results with the *S. warneri* isolate. In aggregate, the results presented in the table represented evidence for the superior accuracy and excellent specificity of the invented probe-based assay.

Example 10

Probes for Detecting Vancomycin Resistance Genes

The sequences of oligonucleotide probes that were used for detecting the VanA and VanB genes are presented below. Of course, because these probes are intended for detecting double-stranded DNA targets, probes having the complements of these sequences also can be used for detecting the VanA and VanB genes, and fall within the scope of the invention. Additionally, detection of mRNA targets falls within the scope of the invention.

```
VanA-specific probes
VanA(+)464
GGGTTGCTCAGAGGAGCATGACGTATCGG      (SEQ ID NO: 27)

VanA(-)792
GCTGAGCTTTGAATATCGCAGCC            (SEQ ID NO: 28)

VanA(-)1325
CGTTCAGTACAATGCGGCCG               (SEQ ID NO: 29)

VanB-specific probes
VanB(+)084
CCGCAGCTTGCATGGACAAATCACTGGC       (SEQ ID NO: 30)

VanB(+)428
CGCATCCATCAGGAAAACGAGCCGG          (SEQ ID NO: 31)

VanB(-)1006
CCAAGCACCCGATATACTTTCTTTGCC        (SEQ ID NO: 32)

VanA and VanB cross-reactive probes
Van A & B(-)734
GAGCTTTGAATATCGCAGCCTAC            (SEQ ID NO: 33)
```

As will be apparent from inspection of these sequences, the VanA(-)792 probe and Van A&B(-)734 probe share a core sequence given by: GAGCTTTGAATATCGCAGCC (SEQ ID NO:34), which is contained within a composite sequence given by GCTGAGCTTTGAATATCGCAGCCTAC (SEQ ID NO:35). The composite represents a contiguous sequence of 26 bases having ends defined by the 5' boundary of the VanA(-)792 probe and by the 3' boundary of the Van A&B (-)734 probe. Each of the two probes has 20 contiguous bases contained within the given composite sequence. Despite the substantial similarities between the VanA(-)792 and Van A&B(-)734 probe sequences, the results presented below proved that the Van A&B(-)734 probe had a superior capacity for either or both of the VanA and VanB gene sequences in lysates derived from clinical samples. This unexpected property could not have been predicted in advance of this showing, and so illustrates one advantage of the Van A&B(-)734 probe. Conversely, the VanA(-)792 probe advantageously was strongly reactive with the VanA gene sequence, and substantially less reactive with the VanB gene sequence, thereby providing a means for selectively detecting the VanA gene sequence in a highly efficient manner.

Each of the above-listed probes was synthesized using DNA precursors, and labeled with acridinium ester by a non-nucleotide linker joined according to the procedures described herein. The linker on the VanA(+)464 probe was located between nucleotide positions 19 and 20. The linker on the VanA(-)792 probe was located between nucleotide positions 8 and 9. The linker on the VanA(-)1325 probe was located between nucleotide positions 13 and 14. The linker on the VanB(+)084 probe was located between nucleotide positions 8 and 9. The linker on the VanB(+)428 probe was located between nucleotide positions 8 and 9. The linker on the VanB (-)1006 probe was located between nucleotide positions 18 and 19. The linker on the Van A&B(-)734 probe was located between nucleotide positions 11 and 12. It should be understood that use of the chemiluminescent AE labeling system merely represents one embodiment of the invention that has been used for illustrative purposes. Other detectable species that will be familiar to those having an ordinary level of skill in the art can be used for labeling the probes. Of course, homogeneously detectable labels represent the most highly preferred detectable labels.

Example 11

Establishing the Genotypes of Cultured VRE Bacteria

Viable samples of VRE bacteria were obtained from the ATCC, propagated on appropriate growth media and their isolated nucleic acids tested by a PCR protocol to determine the identity of the gene responsible for the drug-resistant phenotype. Primers for amplifying the VanA gene had the sequences of VanA(+)464Kpn (CGGGGTACCGGGT-TGCTCAGAGGAGCATGACGTATCGG (SEQ ID NO:36)) and VanA(-)1325Bam (CGCGGATCCGTTCAGTACAAT-GCGGCCG (SEQ ID NO:37)). These primers had the target-complementary sequences of SEQ ID NO:27 and SEQ ID NO:29, respectively, positioned downstream of sequences that were not complementary to the target to be amplified. Primers for amplifying the VanB gene had the sequences of VanB(+)084Kpn (CGGGGTACCGCAGCTTGCATGGA-CAAATCACTGGC (SEQ ID NO:38)) and VanB(-) 1006Bam (CGCGGATCCAAGCAC-CCGATATACTTTCTTTGCC (SEQ ID NO:39)). These primers had the target-complementary sequences of SEQ ID NO:30 and SEQ ID NO:32, respectively, positioned downstream of sequences that were not complementary to the target to be amplified. In every instance, separate reactions were conducted to amplify the VanA and VanB genes using a sample of genomic DNA from each isolate. Positive results indicating the presence of a particular vancomycin-resistance gene were judged by the appearance of a discrete band representing a PCR product on an agarose gel stained with ethidium bromide. Each VRE sample contained either the VanA or VanB gene, and none of the samples contained both genes. The results of these procedures are presented in Table 15.

TABLE 15

Cultured VRE Bacteria Harbor VanA or VanB Gene Sequences

| ATCC # | Species | Genotype |
|---|---|---|
| 51575 | *E. faecalis* | VanB |
| 700221 | *E. faecium* | VanA |
| 700802 | *E. faecalis* | VanB |
| 51299 | *E. faecalis* | VanB |

Example 12

Hybridization Assays for Detecting Genes Encoding Vancomycin Resistance

Double-stranded plasmids harboring inserts of either VanA or VanB gene sequences were prepared for use as control templates. More specifically, VanA gene sequences were amplified in a PCR protocol using primers having the sequences of VanA(+)464Kpn and VanA(−)1325Bam. Similarly, VanB gene sequences were amplified using primers having the sequences of VanB(+)084Kpn and VanB(−)1006Bam. Genomic DNA samples from bacteria known to have VanA or VanB genotypes were used as templates in the amplification reactions. Blunt-ended amplification products containing VanA gene sequences were ligated into a pPCR-SCRIPTAMP SK(+) (Stratagene; La Jolla, Calif.) plasmid cloning vector, and propagated in *E. coli* host bacteria using procedures that will be familiar to those having an ordinary level of skill in the art. Double-stranded amplification products containing VanB gene sequences were first digested with KpnI and BamHI, and then ligated into a similarly cleaved pBLUESCRIPT-II KS(+) (Stratagene; La Jolla, Calif.) plasmid cloning vector. Isolated double-stranded plasmid DNA served as controls in hybridization assays.

2'-deoxy probes having the sequences presented under Example 10 were prepared by standard phosphoramidite synthesis. AE labeling of the probes also was performed using standard procedures, as described herein and as will be familiar to those having an ordinary level of skill in the art. Samples of four different cultured VRE bacteria described under the previous Example were lysed essentially as described above. RNA in the samples was hydrolyzed and DNA denatured by incubation of the lysate with hydroxide at elevated temperature. In parallel procedures, samples of two plasmid clones harboring either the VanA or VanB inserts (as described under the previous Example) were also treated to denature DNA. All samples were neutralized by addition of a buffered HCl reagent. AE-labeled probes were added to each of the samples and then hybridized at 55-60° C. for 45 minutes to permit formation of complementary probe:target duplexes. The pan-bacterial probe (Probe Reagent 1, GEN-PROBE® MTC-NI Kit, catalog no. 4573) described under Example 2 was used as a positive control to confirm the presence of bacterial nucleic acid targets. Trials containing labeled probe in the absence of an added target (i.e., "probe alone") served as negative controls. The AE label joined to probe molecules that remained single-stranded following the hybridization procedure were destroyed by treatment under mild alkaline conditions, and the extent of specific hybrid formation quantified by luminometry as described in the foregoing Examples. Notably, the VanB plasmid clone did not fully contain the sequence complementary to the Van A&B(−)734 probe. Numerical results from these procedures (measured in RLU) are presented in Table 16.

TABLE 16

Detection of VanA and VanB Gene Sequences by Probe Hybridization (in RLU)

| Probe | ATCC 1575 (VanB) | ATCC 700221 (VanA) | ATCC 700802 (VanB) | ATCC 51299 (VanB) | VanA clone | VanB clone | Probe Alone |
|---|---|---|---|---|---|---|---|
| VanA(+)464 | 696 | 10910 | 757 | 765 | 37434 | 817 | 374 |
| VanA(−)792 | 2254 | 10627 | 3653 | 2983 | 52729 | 505 | 256 |
| VanA(−)1325 | 1761 | 23523 | 931 | 1182 | 24378 | 942 | 368 |
| VanA&B(−)734 | 5166 | 8901 | 7425 | 5497 | 48999 | 718† | 240 |
| VanB(+)084 | 6003 | 768 | 10119 | 7863 | 716 | 54711 | 371 |
| VanB(+)428 | 6307 | 683 | 9657 | 8113 | 684 | 49242 | 370 |
| VanB(−)1006 | 6300 | 1485 | 9116 | 8335 | 1708 | 27493 | 586 |
| MTC-NI (+)control | 23497 | 33027 | 68973 | 29585 | 975 | 530 | 297 |

†The VanB plasmid clone does not fully include the complement of the Van A&B(−) 734 probe.

The results presented in Table 16 proved that each of the various probes specific for VanA, VanB, or the combination of VanA and/or VanB was able to detect and identify the appropriate vancomycin-resistance gene present in each of the four cultured bacterial samples. More particularly, the VanA(+)464, VanA(−)792 and VanA(−)1325 probes gave very strong hybridization signals for samples containing nucleic acids from the single bacterial isolate that was VanA-positive. Each of these probes produced substantially weaker signals when hybridized with samples that did not harbor the VanA target. Similarly, the VanB(+)084, VanB(+)428 and VanB(−)1006 probes gave very strong signals when hybridized with samples containing nucleic acids from the VRE bacteria that were VanB-positive. Each of these probes produced substantially weaker signals when hybridized with samples that did not harbor the VanB nucleic acid target. Finally, the Van A&B(−)734 probe gave very strong signals when hybridized with nucleic acids from VRE bacteria that were either VanA-positive or VanB-positive.

Interestingly, the Van A&B(−)734 and VanA(−)792 probes exhibited strikingly different hybridization characteristics despite having target-complementary sequences that are 23 bases in length and sharing a common core sequences of 20 bases. Despite these similarities, the two probes differed from each other in their relative selectivity for VanA and VanB targets, as illustrated by the quantitative results obtained using lysates prepared from the different bacterial isolates. For example, comparison of background-corrected hybridization signals relative to negative controls obtained using the VanA-positive bacterial sample (ATCC #700221) and either of the two probes were substantially comparable (being about 40 fold and about 36 fold greater than background signals for the VanA(−)792 and Van A&B(−)734 probes, respectively). A similar comparison of signals resulting from hybridization of the two probes with lysates of VanB-positive bacterial samples (ATCC Nos. 51575, 700802 and 51299) yielded very different results. In these instances the hybridization signals obtained using the VanA(−)792 probe averaged about 10.5 fold greater than background, while the hybridization signals obtained using the Van A&B(−)734 probe averaged about 24 greater than background. Under a conventional scenario wherein positive results are judged as being at least 10 fold greater than the negative control, the two probes uniformly detected the VanA target, but equivocally detected the VanB target. These findings emphasized the subtle effect of minor sequence variations on probe functionality.

The following Example describes a test device that fulfilled several preferred design goals. The device included a solid support harboring individual wells for containing defined collections of soluble hybridization probes in a spaced-apart configuration. This arrangement meant that all of the probes could be transported simultaneously, for example to a hybridization incubator or luminometer, and that all of the hybridization reactions could conveniently be conducted under the same temperature conditions. The device facilitated rapid identification of *S. aureus*, coagulase-negative Staphylococcal bacteria (CoNS), as well as *Enterococcus* bacteria. Additionally, the device was capable of detecting nucleic acid markers indicative of resistance to methicillin or vancomycin in any organism undergoing testing. Finally, the device was useful for conducting homogeneous assays. Accordingly, it was unnecessary to separate unhybridized probe from specifically hybridized probe in order to detect specific hybrids which indicated the presence of a complementary target sequence.

The fact that the device is preferably used for testing DNA, and not RNA, to determine the presence or absence of the relevant targets imposed certain limitations, and defined a problem to be overcome. More particularly, when the amount of a DNA sample to be tested is limiting, the number of hybridization reactions needed to make the identification must be minimized. A preferred solution to the problem involved combining certain probes in a single hybridization reaction such that a positive hybridization result yielded an ambiguous determination. As described below, rather than conducting separate hybridization reactions using probes specific for the VanA and VanB genes, a single hybridization reaction was used to identify nucleic acids containing either of these targets without determining which target was present. Additionally, two probes that were independently specific for the nucleic acids of *S. aureus* and for *Enterococcus* bacteria harbored identical labels and were combined in a single hybridization reaction. A positive hybridization signal in this reaction indicated the presence of *S. aureus* or *Enterococcus* bacteria, without particularly identifying which organism was present.

When sufficient material is available for testing, the added use of a pan-bacterial probe as a positive control provides additional functionality to the invented device, and eliminates the requirement for foreknowledge about the identity of the organism undergoing testing. For example, because it is easily possible for an organism to be misidentified as a member of the *Enterococcus* group preliminary to testing with the invented device, negative results using an *Enterococcus*-specific hybridization probe (in the absence of a pan-bacterial address), together with negative results at other addresses in the device, would be uninformative because it would be possible that either insufficient material was included in the procedure, or that the organism had been misidentified prior to the probe hybridization procedure. This ambiguity can be overcome by the use of a pan-bacterial probe as a positive control. Accordingly, a positive hybridization signal observed in a hybridization reaction using a pan-bacterial probe of the type described herein will indicate that sufficient nucleic acid is present in the sample undergoing testing to provide meaningful results in the other hybridization reactions conducted using the same device.

Example 13

Device for Conducting Simultaneous Bacterial Identification and Antibiotic Resistance Testing Aliquots of AE-labeled hybridization probes having the following specificities were dispensed into four wells of a 96-well plastic microtiter plate as follows. The first well of the device contained an aliquot of AE-labeled probe having the sequence of SEQ ID NO:10, together with helper oligonucleotides having the sequences of SEQ ID NOs:11 and 12, and so was capable of hybridizing to the nucleic acids of a plurality of bacteria in the *Staphylococcus* genus, including *S. aureus*, *S. epidermidis* and *S. haemolyticus*, but not to the nucleic acids of bacteria in the genus *Enterococcus*. The oligonucleotide having the sequence of SEQ ID NO:11 was synthesized using 2'-methoxy nucleotide analogs. The second well contained a mixture of AE-labeled probes, one of the probes having the *S. aureus*-specific sequence of SEQ ID NO:7, together with helper oligonucleotides having the sequences of SEQ ID NOs:8 and 9. The second well further included a first AE-labeled Enterococcus-specific probe having the sequence of SEQ ID NO:14, together with helper oligonucleotides having the sequences of SEQ ID NOs:23 and 24, and a second AE-labeled *Enterococcus*-specific probe having the sequence of SEQ ID NO:15, together with helper oligonucleotides having the sequences of SEQ ID NOs:25 and 26. The probes in the second well were capable of hybridizing to the nucleic acids of *S. aureus* and *Enterococcus* bacteria. Notably, the probes in the second well did not exhibit cross-reactivity, meaning that the probe specific for the nucleic acids of *S. aureus* did not hybridize to the nucleic acids of *Enterococcus* bacteria, and the probe specific for the nucleic acids of *Enterococcus* bacteria did not hybridize to the nucleic acids of *S. aureus* or any other member of the *Staphylococcus* genus. Also notably, the probe specific for the nucleic acids of *S. aureus* did not hybridize to the nucleic acids of other members of the *Staphylococcus* genus. Thus, the *S. aureus*-specific probe did not hybridize to, for example, *S. epidermidis* or *S. haemolyticus*. The third well of the device contained a mixture of AE-labeled probes having the sequences of SEQ ID NOs:2, 3 and 5, and so was capable of hybridizing to nucleic acids of the mecA gene, but not to the nucleic acids of either the VanA or VanB genes. These three probes were all synthesized using 2'-methoxy nucleotide analogs. The fourth well of the device contained a mixture of AE-labeled probes having the sequences of SEQ ID NOs:27, 28, 29, 30. The mixture further included AE-labeled probes having the complements of SEQ ID NO:31 (i.e., CCG-GCTCGTTTTCCTGATGGATGCG (SEQ ID NO:40)) and SEQ ID NO:32 (i.e., GGCAAAGAAAGTATATCGGGT-GCTTGG (SEQ ID NO:41)). The probes in the fourth well were capable of hybridizing to the nucleic acids of the VanA and VanB genes, but not to the nucleic acids of the mecA gene. As indicated above, an optional fifth well of the device can contain a labeled probe that specifically hybridizes to the nucleic acids of a plurality of bacterial organisms, but not to the nucleic acids of fungal organisms. For example, a labeled probe having the sequence of SEQ ID NO:16 may be used for this purpose.

Numerous biological samples were tested using the sample preparation, probe hybridization and specific-hybrid detection methods described herein. The results uniformly conformed to the patterns of positive and negative hybridization results presented in Table 17. Indeed, when the device was used for hybridizing nucleic acids of a test organism, it was possible to determine the identity of the donor organism from the unique combination of positive and negative hybridization results using the information shown in the table. Notably, filled boxes in Table 17 indicate positive hybridization signals, and open boxes indicate the absence of a positive hybridization signal. Entries in the table for MRE (methicillin-resistant *Enterococcus*) and VRSA (vancomycin-resistant *S. aureus*) show the unique patterns of hybridization results that would be expected for these isolates, although these organisms were not available for testing. Since many VRSA isolates are also resistant to methicillin, bacteria having the dual antibiotic resistant phenotype would be expected to give positive hybridization signals at the mecA address, as well as at the VanA and/or VanB addresses. Methicillin-resistant CoNS isolates would be expected to give positive hybridization signals at the *Staphylococcus* genus address and at the mecA address, but not at the *S. aureus/Enterococcus* address or at the VanA/VanB address. Finally, all of the probes used in the device were hybridized at the same temperature to achieve the results presented in the following table.

TABLE 17

Decoding Hybridization Results for Bacterial Identification and Antibiotic Resistance Testing

| Probe Address | Hybridization Result and Corresponding Interpretation | | | | | | |
| --- | --- | --- | --- | --- | --- | --- | --- |
| | *S. aureus* | CoNS | *Enterococcus* | MRE | VRE | MRSA | VRSA |
| *Staphylococcus* genus | ■ | ■ | | | | ■ | ■ |
| *S. aureus* and *Enterococcus* genus | ■ | | ■ | ■ | ■ | ■ | ■ |
| mecA | | | | ■ | | ■ | ■ |
| VanA and VanB | | | | | ■ | | ■ |

An alternative approach for obtaining diagnostic information substantially equivalent to that presented in the foregoing table involves the use of six independent probe addresses. Table 18 shows the results that would be expected if hybridization reactions were conducted using the same hybridization probes and procedures as described above, with the exception that each hybridization reaction yielded an unambiguous result. To illustrate this aspect of the invention, the VanA and VanB results are shown in Table 18 as being coincident for the VRE and VRSA addresses for the vancomycin-resistant phenotypes. However, one (but not both) of the VanA and VanB addresses could give a negative hybridization result and still indicate a vancomycin-resistant phenotype. Stated differently, if either the VanA or VanB probe address gave a positive hybridization signal, that would be evidence for resistance to vancomycin. As indicated above, because many VRSA isolates are also resistant to methicillin, bacteria having the dual antibiotic resistant phenotype would be expected to give positive hybridization signals at the mecA address, as well as at the VanA and/or VanB addresses. Methicillin-resistant CoNS isolates would give positive hybridization signals at the *Staphylococcus* genus address and at the mecA address, but not at addresses for detecting the nucleic acids specific for *S. aureus, Enterococcus*, VanA or VanB.

TABLE 18

Decoding Hybridization Results for Bacterial Identification and Antibiotic Resistance Testing

| Probe Address | Hybridization Result and Corresponding Interpretation | | | | | | |
| --- | --- | --- | --- | --- | --- | --- | --- |
| | *S. aureus* | CoNS | *Enterococcus* | MRE | VRE | MRSA | VRSA |
| *Staphylococcus* genus | ■ | ■ | | | | ■ | ■ |
| *S. aureus* | ■ | | | | | ■ | ■ |
| *Enterococcus* genus | | | ■ | ■ | ■ | | |
| mecA | | | | ■ | | ■ | ■ |
| VanA | | | | | ■ | | ■ |
| VanB | | | | | ■ | | ■ |

Finally, using the above-described hybridization assay techniques, it is possible to quantify the contributions of mixtures of different organisms based on the magnitudes of the measured hybridization signals.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A device for detecting nucleic acids encoding resistance to an antibiotic, comprising a solid support and a plurality of detectably labeled solution-phase hybridization probes distributed among a plurality of loci thereon, said plurality of loci comprising,
   (a) a first locus that comprises one or more solution-phase hybridization probes that collectively hybridize to ribosomal nucleic acids from a plurality of species of bacteria in the genus *Staphylococcus*, comprising *Staphylococcus aureus* and *Staphylococcus epidermidis*, but do not hybridize to ribosomal nucleic acids of bacteria in the genus *Enterococcus*,
   (b) a second locus that comprises a probe mix containing
      (i) one or more solution-phase hybridization probes that collectively hybridize to ribosomal nucleic acids from a plurality of bacteria in the genus *Enterococcus*, comprising *Enterococcus faecalis* and *Enterococcus faecium*, but not *Staphylococcus aureus* or any other bacteria in the genus *Staphylococcus*, and
      (ii) at least one solution-phase hybridization probe that hybridizes to ribosomal nucleic acids from *Staphylococcus aureus* but not from other species in the genus *Staphylococcus* or bacteria in the genus *Enterococcus*,
   (c) a third locus that comprises a probe mix containing a first mecA solution-phase hybridization probe that consists of the nucleotide sequence of SEQ ID NO:2 or the complement thereof, a second mecA solution-phase hybridization probe that consists of the nucleotide sequence of SEQ ID NO:3 or the complement thereof, and a third mecA solution-phase hybridization probe that consists of the nucleotide sequence of SEQ ID NO:5 or the complement thereof, and
   (d) a fourth locus that comprises a solution-phase hybridization probe that hybridizes both to VanA nucleic acids and VanB nucleic acids, wherein said solution-phase hybridization probe consists of the nucleotide sequence of SEQ ID NO:33 or the complement thereof; wherein each of said plurality of loci is configured as a matrix that provides an identification of one or more unknown nucleic acids from a sample, and wherein each of said detectably labeled solution-phase hybridization probes comprises a polynucleotide sequence which is covalently attached to a non-nucleotide detectable moiety that emits a detectable signal.

2. The device of claim 1, wherein said non-nucleotide detectable moiety is a homogeneously detectable label.

3. The device of claim 2, wherein said homogeneously detectable label is a chemiluminescent label.

4. The device of claim 1, further comprising a fifth locus, said fifth locus comprising one or more solution-phase hybridization probes that collectively hybridize to ribosomal nucleic acids from a plurality of species of Gram-positive bacteria comprising the high(G+C) subset thereof, a plurality of species of bacteria in the family *Enterobacteriaceae*, a plurality of species of bacteria in the genus *Enterococcus*, and a plurality of species of bacteria in the genus *Staphylococcus*.

5. The device of claim 1, wherein the first mecA solution-phase hybridization probe of said probe mix consists of the nucleotide sequence of SEQ ID NO:2, wherein the second mecA solution-phase hybridization probe of said probe mix consists of the nucleotide sequence of SEQ ID NO:3, and wherein the third mecA solution-phase hybridization probe of said probe mix consists of the nucleotide sequence of SEQ ID NO:5.

6. The device of claim 1, wherein each of said plurality of detectably labeled solution-phase hybridization probes comprises the non-nucleotide detectable moiety prior to contact with a biological sample to be tested for the presence of microorganisms or nucleic acids thereof.

7. The device of claim 1, wherein said plurality of loci are wells of a multi-well plate.

8. A kit for differentiating between bacteria, wherein said kit comprises the device of claim 1.

9. The kit of claim 8, wherein said kit comprises one or more of, a specimen lysis reagent; a probe hybridization reagent; a selection reagent; an alkaline hydrolysis reagent; or an internal control nucleic acid.

10. A device for detecting nucleic acids encoding resistance to an antibiotic, comprising a solid support and a plurality of detectably labeled solution-phase hybridization probes distributed among a plurality of loci thereon, said plurality of loci comprising,
 (a) a first locus that comprises one or more solution-phase hybridization probes that collectively hybridize to ribosomal nucleic acids from a plurality of bacteria in the genus *Enterococcus*, comprising *Enterococcus faecalis* and *Enterococcus faecium*,
 (b) a second locus that comprises a solution-phase hybridization probe that hybridizes to both VanA nucleic acids and to VanB nucleic acids, wherein said solution-phase hybridization probe consists of the nucleotide sequence of SEQ ID NO:33 or the complement thereof, and
 (c) a third locus that comprises one or more solution-phase hybridization probes that collectively hybridize to ribosomal nucleic acids from a plurality of species of Gram-positive bacteria comprising the high (G+C) subset thereof, a plurality of species of bacteria in the family *Enterobacteriaceae*, a plurality of species of bacteria in the genus *Enterococcus*, and a plurality of species of bacteria in the genus *Staphylococcus;* wherein each of said plurality of loci is arranged as a matrix for identification of one or more soluble unknown nucleic acids from a sample, and wherein each of said detectably labeled solution-phase hybridization probes comprises a polynucleotide sequence which is covalently attached to a non-nucleotide detectable moiety that emits a detectable signal.

11. The device of claim 10, wherein said one or more solution-phase hybridization probes of said third locus comprise a pan-bacterial probe of SEQ ID NO:16.

12. The device of claim 10, wherein each of said plurality of detectably labeled solution-phase hybridization probes comprises the non-nucleotide detectable moiety prior to contact with a biological sample to be tested for the presence of microorganisms or nucleic acids thereof.

13. The device of claim 10, wherein said plurality of loci are wells of a multi-well plate.

14. A kit for differentiating between bacteria, wherein said kit comprises the device of claim 10.

15. The kit of claim 14, wherein said kit comprises one or more of, a specimen lysis reagent; a probe hybridization reagent; a selection reagent; an alkaline hydrolysis reagent; or an internal control nucleic acid.

\* \* \* \* \*